US010806735B2

(12) United States Patent
Satyal et al.

(10) Patent No.: US 10,806,735 B2
(45) Date of Patent: Oct. 20, 2020

(54) USE OF NEUTROPHIL ELASTASE INHIBITORS IN LIVER DISEASE

(71) Applicant: pH Pharma Co., Ltd., Seoul (KR)

(72) Inventors: Sanjeev Satyal, San Carlos, CA (US); Brian Roberts, Danville, CA (US); Xueyan Wang, Foster City, CA (US); Scott Savage, Redwood City, CA (US); Hoyoung Huh, Portola Valley, CA (US)

(73) Assignee: pH Pharma Co., Ltd., Seoul (KR)

( * ) Notice: Subject to any disclaimer, the term of this patent is extended or adjusted under 35 U.S.C. 154(b) by 0 days.

(21) Appl. No.: 16/390,970

(22) Filed: Apr. 22, 2019

(65) Prior Publication Data

US 2019/0321364 A1    Oct. 24, 2019

Related U.S. Application Data

(60) Provisional application No. 62/662,074, filed on Apr. 24, 2018.

(51) Int. Cl.
*A61K 31/513* (2006.01)
*A61P 1/16* (2006.01)
*A61K 9/20* (2006.01)

(52) U.S. Cl.
CPC .............. *A61K 31/513* (2013.01); *A61K 9/20* (2013.01); *A61P 1/16* (2018.01)

(58) Field of Classification Search
CPC ...... A61K 31/513; A61K 9/20; A61K 9/2054; A61P 1/16
See application file for complete search history.

(56) References Cited

U.S. PATENT DOCUMENTS

| | | | |
|---|---|---|---|
| 8,288,402 B2 | 10/2012 | Von Nussbaum et al. | |
| 8,889,700 B2 | 11/2014 | Von Nussbaum et al. | |
| 9,174,997 B2 | 11/2015 | Von Nussbaum et al. | |
| 10,316,001 B2 | 6/2019 | Schirmer et al. | |
| 2016/0031829 A1 | 2/2016 | Oost et al. | |
| 2018/0072685 A1 | 3/2018 | Schirmer et al. | |

FOREIGN PATENT DOCUMENTS

| | | |
|---|---|---|
| WO | 2009080199 A1 | 7/2009 |
| WO | 2016050835 A3 | 6/2016 |
| WO | 2016146607 A1 | 9/2016 |
| WO | 2017081044 A1 | 5/2017 |

(Continued)

OTHER PUBLICATIONS

Clinical Trials (https://clinicaltrials.gov/ct2/history/NCT02970942?V_12=View#StudyPageTop, accessed Oct. 17, 2019, published Mar. 23, 2017 (Year: 2017).*

(Continued)

*Primary Examiner* — Angela C Brown-Pettigrew
(74) *Attorney, Agent, or Firm* — Viksnins Harris Padys Malen LLP; Alexandra J. Baran

(57) ABSTRACT

The invention relates to methods for treating chronic liver disease, in particular nonalcoholic fatty liver disease (NAFLD) and nonalcoholic steatohepatitis (NASH), with neutrophil elastase inhibitors. The invention further relates to pharmaceutical compositions comprising neutrophil elastase inhibitors.

4 Claims, 11 Drawing Sheets

(56) References Cited

FOREIGN PATENT DOCUMENTS

WO            2017194975 A1    11/2017

OTHER PUBLICATIONS

Alkhouri, N , et al., "Neutrophil to lymphocyte ratio: a new marker for predicting steatohepatitis and fibrosis in patients with nonalcoholic fatty liver disease", Liver International 32(2), 297-302 (2012).
Crocetti, L , et al., "1H-pyrrolo [2, 3-b] pyridine: A new scaffold for human neutrophil elastase (HNE) inhibitors", Bioorganic & Medicinal Chemistry 26(21), 5583-5595 (2018).
Elgazar-Carmon, V , et al., "Neutrophils transiently infiltrate intra-abdominal fat early in the course of high-fat feeding", J Lipid Research 49, 1894-1903 (2008).
Feurer, M , et al., "Lean, but not obese, fat is enriched for a unique population of regulatory T cells that affect metabolic parameters", Nature Medicine 15, 930-939 (2009).
Gadd, V , et al., "The portal inflammatory infiltrate and ductular reaction in human nonalcoholic fatty liver disease", Hepatology 59(4), 1393-1405 (2014).
Hansen, H , et al., "Mouse models of nonalcoholic steatohepatitis in preclinical drug development", Drug Discovery Today 22(11), 1707-1718 (2017).
Houghton, A , et al., "Neutrophil Elastase-Mediated Degradation of IRS-1 Accelerates Lung Tumor Growth", Nature Med 16(2), 219-223 (2010).
Houghton, A , "The paradox of tumor-associated neutrophils: fueling tumor growth with cytotoxic substances", Cell Cycle 9(9), 1732-1737 (2010).
Liu, J , et al., "Genetic deficiency and pharmacological stabilization of mast cells reduce diet-induced obesity and diabetes in mice", Nature Medicine 15, 940-945 (2009).
Mansuy-Aubert, V , et al., "Imbalance between neutrophil elastase and its inhibitor α1-antitrypsin in obesity alters insulin sensitivity, inflammation, and energy expenditure", Cell Metabolism 17, 535-548 (2013).
Nagelschmitz, J , et al., "The novel elastase inhibitor BAY 85/8501: Bioavailability and Food effect study to evaluate pharmacokinetics of tablet formulations", European Respiratory J 44, P1511 (2014).
Nagelschmitz, J , et al., "The novel elastase inhibitor BAY 85-8501: First-in-man study to evaluate safety, tolerability and pharmacokinetics in healthy male subjects", European Respiratory J 44 (Suppl 58), P1510, (2014).
Nishimura, S , et al., "CD8+ effector T cells contribute to macrophage recruitment and adipose tissue inflammation in obesity", Nature Medicine 15(8), 914-920 (2009).
Osborn, O , et al., "The cellular and signaling networks linking the immune system and metabolism in disease", Nature Medicine 18(3), 363-374 (2012).
Ouchi, N , et al., "Adipokines in inflammation and metabolic disease", Nature Reviews Immunol 11, 85-97 (2011).
Patent Cooperation Treaty , International Searching Authority, Search Report and Written Opinion for PCT/US2019/28551, 9 pages, dated Aug. 6, 2019.
Rensen, S , et al., "Increased hepatic myeloperoxidase activity in obese subjects with nonalcoholic steatohepatitis", Am J Pathol 175, 1473-1482 (2009).
Sun, S , et al., "Mechanisms of inflammatory responses in obese adipose tissue", Annul Rev Nutr 32, 261-286 (2012).
Talukdar, S , et al., "Neutrophils mediate insulin resistance in mice fed a high-fat diet through secreted elastase", Nature Medicine 18(9), 1407-1412 (2012).
Von Nussbaum, F , et al., "Freezing the Bioactive Conformation to Boost Potency: The Identification of BAY 85-8501, a Selective and Potent Inhibitor of Human Neutrophil Elastase for Pulmonary Diseases", ChemMedChem 10, 1163-1173 (2015).
Von Nussbaum, F , et al., "Potent and Selective Human Neutrophil Elastase Inhibitors with Novel Equatorial Ring Topology: in vivo Efficacy of the Polar Pyrimidopyridazine BAY-8040 in a Pulmonary Arterial Hypertension Rat Model", ChemMedChem 11(2), 199-206 (2016).
Watz, H , et al., "Safety and efficacy of the human neutrophil elastase inhibitor BAY 85-8501 for the treatment of non-cystic fibrosis bronchiectasis: A randomized controlled trial", Pulmonary Pharmacology & Therapeutics 56, 86-93 (2019).
Watz, H , et al., "Safety and tolerability of the NE inhibitor BAY 85-8501 in patients with non-CF bronchiectasis", European Respiratory J 48, PA4088 (2016).
Weisberg, S , et al., "Obesity is associated with macrophage accumulation in adipose tissue", J Clin Invest 112, 1796-1808 (2003).
Winer, D , et al., "B cells promote insulin resistance through modulation of T cells and production of pathogenic IgG antibodies", Nature Medicine 17, 610-618 (2011).
Xu, J , et al., "Chronic inflammation in fat plays a crucial role in the development of obesity-related insulin resistance", J Clin Invest 112, 1821-1830 (2003).
Zang, S , et al., "Sivelestat alleviates nonalcoholic steatohepatitis in mice through inhibiting activation of Kupffer cells", Chinese J Hepatology 25(5), 371-376 (2017). [English Abstract].
Zang, S , et al., "Increased ratio of neutrophil elastase to α1-antitrypsin is closely associated with liver inflammation in patients with nonalcoholic steatohepatitis", Clinical and Experimental Pharmacology and Physiology 43, 13-21 (2015).
Zang, S , et al., "Neutrophils Play a Crucial Role in the Early Stage of Nonalcoholic Steatohepatitis via Neutrophil Elastase in Mice", Cell Biochem Biophys 73, 479-487 (2015).
Berman, A , et al., "The therapeutic potential of resveratrol: a review of clinical trials", npl Precision Oncology 1(35), 9 pages, doi: 10.1038/s41698-017-0038-6 (2017).
Choi, Y , et al., "Seladelpar Improves Hepatic Steatohepatitis and Fibrosis in a Diet-Induced and Biopsy-Confirmed Mouse Model of NASH", AASLD, The Liver Meeting, Abstract #1311, San Francisco, CA, Nov. 9-13, 2018.
Harrison, S , et al., "Selonsertib for Patients with Bridging Fibrosis or Compensated Cirrhosis Due to NASH: Results from Randomized Ph III STELLAR Trials", Journal of Hepatology 46 pages, doi: https://doi.org/10.1016/j.jhep.2020.02.027 (2020).
Jahn, D , et al., "Animal models of NAFLD from a hepatologist's point of view", Bbadis, doi:10.1016/j.bbadis.2018.06.023, 39 pages (2018).
Kawabata, K , et al., "ONO-5046, A Novel Inhibitor of Human Neutrophil Elastase", Biochemical and Biophysical Research Communications 177(2), 7 pages (1991).
Liang, W , et al., "Establishment of a General NAFLD Scoring System for Rodent Models and Comparison to Human Liver Pathology", PLOS One 9(12), e115922, 17 pages (2014).
Nakade, Y , et al., "Ezetimibe for the treatment of nonalcoholic fatty liver disease: a meta-analysis", doi: 10.1111/hepr.12887, 26 pages (2017).
Van Herck, M , et al., "Animal Models of Nonalcoholic Fatty Liver Disease—A Starter's Guide", Nutrients 9, 1072, 13 pages (2017).
Von Nussbaum, F , et al., "Neutrophil elastase inhibitors for the treatment of (cardio) pulmonary diseases: Into clinical testing with pre-adaptive pharmacophores", Bioorganic & Medicinal Chemistry Letters 25, 4370-4381 (2015).

\* cited by examiner

A

B

C

D

C

D

A

B

USE OF NEUTROPHIL ELASTASE INHIBITORS IN LIVER DISEASE

CROSS REFERENCE TO RELATED APPLICATIONS

This application is a non-provisional application, claiming priority under 35 U.S.C. § 119(e) to provisional application Ser. No. 62/662,074, filed Apr. 24, 2018, the contents of which is herein incorporated by reference in its entirety.

TECHNICAL FIELD

The invention relates to methods for treating chronic liver disease, in particular nonalcoholic fatty liver disease (NAFLD) and nonalcoholic steatohepatitis (NASH), with neutrophil elastase inhibitors. The invention further relates to pharmaceutical compositions comprising neutrophil elastase inhibitors.

BACKGROUND OF THE INVENTION

Nonalcoholic fatty liver disease (NAFLD) refers to a group of increasingly serious liver disorders ranging from hepatocellular steatosis through nonalcoholic steatohepatitis (NASH) to fibrosis, and irreversible cirrhosis. Paralleling the obesity and diabetes epidemics, NAFLD/NASH is now the most common cause of chronic liver disease in the Western world and will likely become the leading cause of liver transplants within the next one to two decades (Staels, B., et al., *Hepatology*, 2013, 58:1941-1952; Charlton. M. R., et al., *Gastroenterology*, 2011, 141:1249-1253). Insulin-resistance and the resultant hepatic lipid accumulation (steatosis) are widely believed to be the primary pathophysiologic insults in NAFLD/NASH. Inflammation leading to liver cell injury (steatohepatitis) and fibrosis are thought to be important additional pathophysiologic insults that characterize the progression of disease from NAFLD to NASH and ultimately cirrhosis (Chalasani, N., et al., *Hepatology*, 2012, 55(6):2005-2023; Anderson, N. and Borlak, J., *Pharmaological Reviews*, 2008, 60:311-357).

At present, there are no approved therapies for NAFLD/NASH. This situation is surprising given that these conditions were first described over thirty-five years ago and that researchers worldwide have been intensely studying the pathophysiology and diagnosis of these diseases for over fifteen years (Ratzui, V., et al., *J. Hepatology*, 2015, 62:S65-S75). Ratzui et al. have speculated that liver steatosis was historically considered a benign condition observed in diabetics without clinical relevance and that pharmaceutical research consequently focused on anti-diabetic drugs (Ratzui 2015). The more serious effects of NAFLD/NASH have now been appreciated, and given the increasing incidence of these diseases, a need for safe and effective treatment exists.

SUMMARY OF THE INVENTION

In one aspect, this invention provides a method of treating chronic liver disease, comprising administering a therapeutically effective amount of (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof to a patient in need of treatment. In one embodiment, the chronic liver disease is nonalcoholic fatty liver disease (NAFLD). In another embodiment, the chronic liver disease is nonalcoholic steatohepatitis (NASH). In a further embodiment, the therapeutically effective amount comprises a dosage of 1 mg, 2 mg, 5 mg, 10 mg, or 20 mg once a day. In another embodiment, the method of treating chronic liver disease further comprises administering one or more additional therapeutic agents. In one embodiment, the additional therapeutic agent is a neutrophil elastase inhibitor. In a further embodiment, the neutrophil elastase inhibitor is silevestat or avelestat. In another embodiment, the additional therapeutic agent treats or ameliorates NAFLD or NASH via a mechanism other than inhibition of neutrophil elastase. In a further embodiment, the additional therapeutic agent is GFT505, seladelpar, cenecriviroc, GS-0976, GS-9674, selonsertib, or obeticholic acid. In another embodiment, the additional therapeutic agent is an anti-diabetes agent. In a further embodiment, the anti-diabetes agent is pioglitazone, rosiglitazone, liraglutide, dulaglutide, semaglutide, canagliflozin, empagliflozin, luseogliflozin, or ipragliflozin.

In another aspect, this invention provides a pharmaceutical composition for the treatment of chronic liver disease comprising (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof and a pharmaceutically acceptable carrier. In one embodiment, the pharmaceutical composition is formulated as a tablet. In another embodiment, the tablet comprises (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof and one or more diluents, disintegrants, surfactants or lubricants. In a further embodiment, the pharmaceutical composition comprises 1 mg, 2 mg, 5 mg, 10 mg, or 20 mg of (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof.

In another aspect, this invention provides a method of treating chronic liver disease in a patient in need of such treatment comprising administering to said patient a therapeutically effective amount of a pharmaceutical composition comprising (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof and a pharmaceutically acceptable carrier. In one embodiment, the chronic liver disease is NAFLD. In another embodiment, the chronic liver disease is NASH. In a further embodiment, the pharmaceutical composition comprises 1 mg, 2 mg, 5 mg, 10 mg, or 20 mg of (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof.

Other objects of the invention may be apparent to one skilled in the art upon reading the following specification and claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
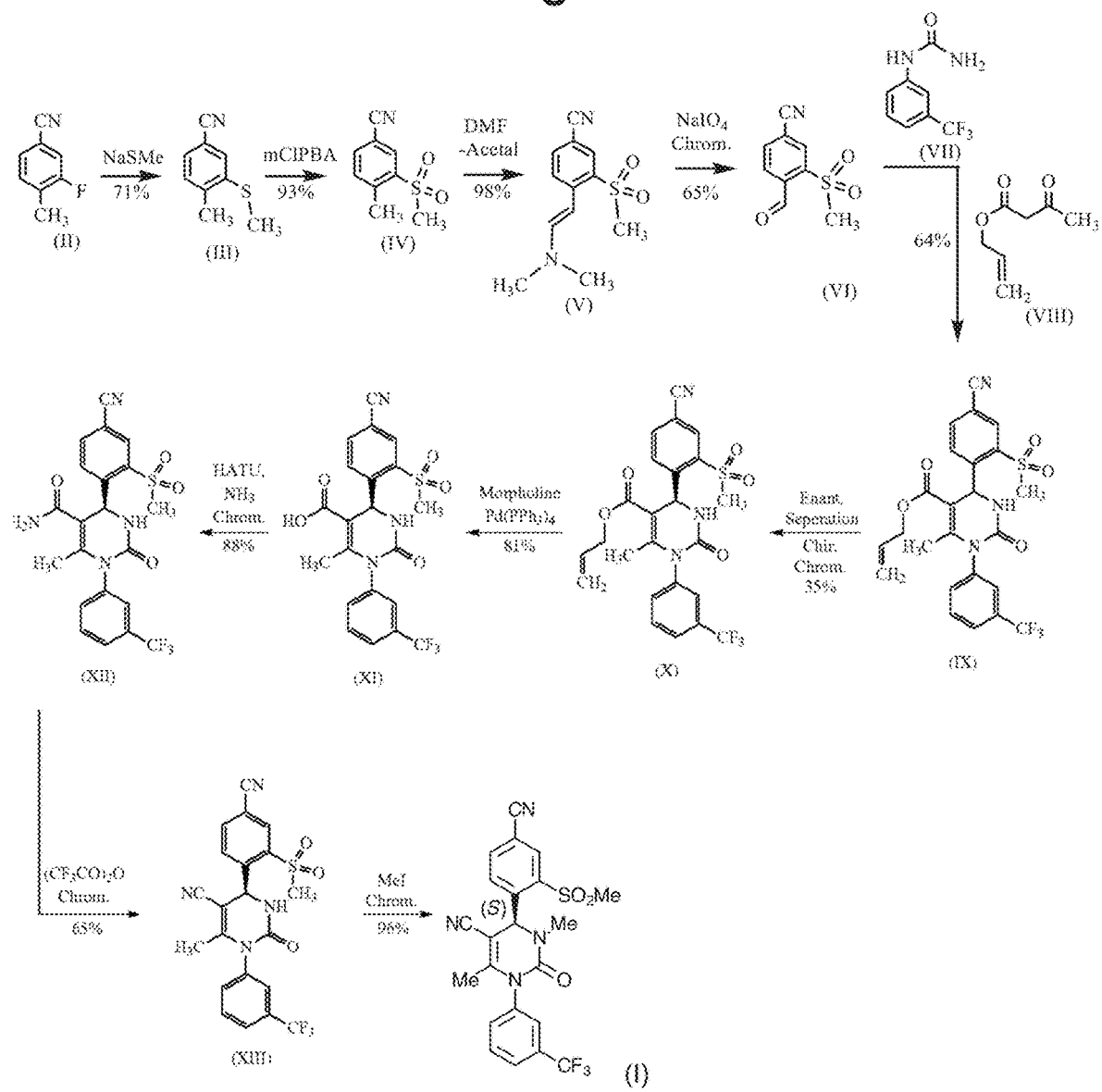
FIG. 1 shows the total synthesis of (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile as described in U.S. Pat. No. 8,288,402 (Von Nussbaum). The reaction scheme is as follows: the reaction sequence from a compound of formula (II) through the compounds of formula (III), (IV) and (V) to a compound of formula (VI) in Scheme 6 and Examples 1A, 2A Method B, and 3A Method B and 4A Method B of the Von Nussbaum patent; the reaction-sequence from a compound of formula (VI) through a compound of formula (IX) to a compound of formula (X) in Scheme 1 and Examples 3 and 4 of the Von Nussbaum patent; and the reaction sequence from a compound of formula (X) through the compounds of formulas (XI) and (XII) to a compound of (XIII) in Scheme 2 and Examples 5A, 5 and 6 of the Von Nussbaum patent. The synthesis of the compound of formula (I) (Compound 1 herein) is described in Example 33 Method B of the Von Nussbaum patent.

This application is not limited to particular methodologies or the specific compositions described, because the scope of the present application will be limited only by the appended claims and their equivalents. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this application belongs. It must be noted that as used herein and in the appended claims, the singular forms "a", "and", and "the" include plural referents unless the context clearly dictates otherwise.

Reference will now be made in detail to certain preferred methods of treatment, compounds and methods of administering these compounds. The invention is not limited to those preferred compounds and methods, but rather is defined by the claim(s) issuing herefrom.

INTRODUCTION

The present invention provides a method for treating chronic liver diseases, particularly nonalcoholic fatty liver disease (NAFLD) and nonalcoholic steatohepatitis (NASH), using Compound 1, (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof. The present invention also provides pharmaceutical compositions of Compound 1 suitable for use in the treatment of NAFLD and NASH.

Compound 1 has previously been disclosed as a potent neutrophil elastase (NE) inhibitor (Nagelschmitz, J., et al., *European Respiratory J.*, 2014, 44, Suppl. 58, Abstract no. 3416). It is approximately 100 times more selective for human neutrophil elastase ($K_i$ [M]=8.0×10$^{-11}$) than for murine neutrophil elastase ($K_i$ [M]=8.0×10$^{-11}$) (Von Nussbaum, F., et al., *Chem Med Chem.*, 2015, 10:1163-1173), Human neutrophil elastase (hNE, NE) is a very active serine protease secreted by neutrophils during inflammation. It is also known as human leukocyte elastase (HLE, EC 3.4.21.37), This proteolytic enzyme is found in the azurophilic granules of polymorphonuclear leukocytes (PMN leukocytes). The intracellular elastase plays an important role in defense against pathogens by breaking down foreign particles which are taken up through phagocytosis (Nagelschmitz, 2014). The highly active proteolytic enzyme is able to break down a multitude of connective tissue proteins, such protein elastin, collagen and fibronectin. Elastin occurs in high concentrations in all tissue types exhibiting high elasticity, such as in the lungs and in arteries. NE is also an important modulator of inflammatory processes. An excess of hNE activity has been implicated in the pathogenesis of inflammatory pulmonary diseases like bronchiectasis, COPD and pulmonary hypertension.

Compound 1 has been disclosed as a treatment for various pulmonary diseases and for the treatment of chronic wounds in a number of patents and applications (U.S. Pat. Nos. 8,288,402; 8,889,700; 9,174,997; PCT Publication WO 2017/081044), the disclosures of which are herein incorporated by reference).

The safety and tolerability of Compound 1, also known as BAY 85-8501, has been evaluated in several human clinical trials. Four clinical studies, including two Phase 1, single-dose studies in healthy subjects, a Phase 1, multiple-dose study in healthy subjects, and a Phase 2a, multiple-dose study in subjects with non-cystic fibrosis bronchiectasis (nCF BE), have assessed the safety, pharmacokinetics (PK), and pharmacodynamics (PD) of Compound 1 administered as an oral solution and/or an immediate-release (IR) tablet. In healthy subjects participating in the three Phase 1 studies, single and repeated Compound 1 treatments administered at doses up to 1 mg for up to 14 days were safe and well tolerated. Adverse events (AEs) reported in the Phase 1 studies were generally mild and unrelated to study treatment, and no serious AEs (SAEs) were reported. No safety signals for study drug-induced laboratory or ECG abnormalities were observed. (See: Nagleschmitz, J., et al., *European Respiratory J.*, 2014, 44:3416: Nagelschmitz, J., et al., *European Respiratory J.*, 2014, 44:P1511).

A multi-center, Phase 2a, randomized, double-blind, placebo-controlled study in subjects with non-CF BE was conducted using a 28-day oral administration of Compound 1 (www.clinicaltrials.gov: Identifier: NCT01818544). Ninety-four patients (mean age, 66 years, 53% male) were randomized to treatment with 45 patients receiving a 1.0 mg oral dose of Compound 1 administered as an IR tablet. The drug was generally safe and well tolerated over 28 days. Safety results for subjects receiving Compound 1 and placebo were generally similar. AEs were generally mild or moderate in severity, unrelated to study treatment, and not different between study drug and placebo. The incidence of SAEs and withdrawals of study treatment due to AEs was low and no SAEs were attributed by the investigator to the drug. No safety signals for study drug-induced laboratory parameter or ECG effects were observed. (See: Watz, H., et al., *European Respiratory J.*, 2016, 48:PA4088).

Chemical Description

Compound 1, (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile, has the following chemical structure:

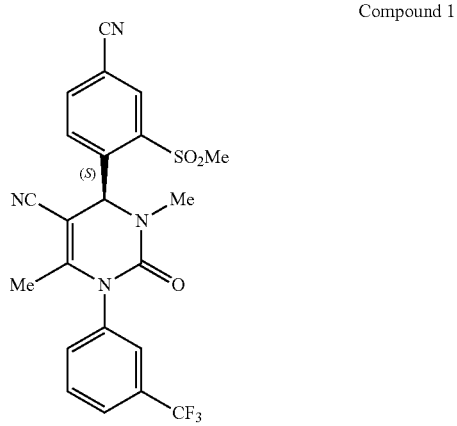

Compound 1

Alternatively, Compound 1 may be named (4S)-4-[4-cyano-2-(methylsulfonyl)phenyl]-1,2,3,4-tetrahydro-3,6-dimethyl-2-oxo-1-[3-(trifluoromethyl)phenyl]-5-pyrimidinecarbonitrile, Compound 1 is commonly known in the literature as BAY 85-8501. It is understood that any of these designations for Compound 1 may be interchangeably used and have the same meaning.

Compound 1 and its salts, polymorphs, solvates, or solvates of salts may exist in various stereoisomeric forms, i.e. in the form of configurational isomers or, if appropriate, also as conformational isomers (enantiomers and/or diastereomers, including atropisomers). Compound 1 therefore also refers to the enantiomers and diastereomers and to their respective mixtures. The stereoisomerically pure constituents can be isolated in a known manner from such mixtures of enantiomers and/or diastereomers, Compound 1 also encompasses any possible tautomeric forms.

Compound 1 may exist in multiple physical forms, including but not limited to, multiple crystalline forms, non-crystalline amorphous forms, and polymorphs. In general, all physical forms are equivalent for the uses contemplated herein and are intended to be within the scope of the present disclosure. Polymorphism refers to the ability of a molecule to exist in two or more crystalline forms in which the molecules with a crystal lattice may differ in structural arrangement and/or conformation. Polymorphic structures have the same chemical composition, although their different lattice structures and/or conformations can result in different physical, chemical or pharmacological properties, such as solubility, stability, melting point, density and bioavailability. Amorphous forms do not have a defined crystal structure. All polymorphs and other physical forms of Compound 1 are equivalent for the uses contemplated herein and are intended to be within the scope of the present invention.

Salts which are preferred for the purposes of the present invention are physiologically acceptable salts of Compound 1. Also encompassed are salts which are themselves unsuitable for pharmaceutical uses but can be used, for example, for isolating or purifying the compounds according to the invention. Salts may exist in multiple physical forms, including but not limited to, multiple crystalline forms, non-crystalline amorphous forms, and polymorphs.

Physiologically acceptable salts of Compound 1 include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, formic acid, fumaric acid, maleic acid and benzoic acid. Physiologically acceptable salts of Compound 1 also include salts of conventional bases such as, by way of example and preferably, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of Compound 1 according to the invention which form, in the solid or liquid state, a complex by coordination with solvent molecules. Solvates may exist in multiple physical forms, including but not limited to, multiple crystalline forms, non-crystalline amorphous forms, and polymorphs. Solvates may also form with the pharmaceutically acceptable salts of Compound 1. Hydrates are a specific form of solvates in which the coordination takes place with water. Various organic solvents may form solvates with Compound 1, including but not limited to, 1,4-dioxane, 1-propanol, 1-butanol, 1,2-dimethoxyethane, 2-ethoxyethanol, 2-methoxyethanol, 2-methyl-1-propanol, 2-methyl tetrahydrofuran, 3-methyl-1-butanol, acetic acid, acetone, acetonitrile, anisole, butyl acetate, chlorobenzene, cumene, dimethylsulfoxide, ethanol, ethyl acetate, ethyl ether, ethyl formate, ethylene glycol, formic acid, heptane, isobutyl acetate, isopropyl ether, isopropyl acetate, methanol, methyl acetate, methyl ethyl ketone, methylisobutyl ketone, N-methylpyrrolidone, tert-butanol, tert-butylmethyl ether, tetrahydrofuran and toluene, Chemical Synthesis Compound 1, (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile, may be prepared as described by Von Nussbaum et al. (U.S. Pat. No. 8,288,402), which is herein incorporated by reference in its entirety. Alternatively, the method of Schirmer et al., as described in U.S. Published Application No. 2018/0072685, which is herein incorporated by reference in its entirety, may be used.

The method of Von Nussbaum et al. is depicted in U.S. Pat. No. 8,288,402. Starting from 3-fluoro-4-methylbenzonitrile, Compound 1 is produced in 10 steps with a total yield of 4.45% of theory. FIG. 1 shows in detail the intermediate steps in the synthesis. The final step is the N-methylation followed by column chromatography. The S-enantiomer is obtained by concentration of chromatography fractions as an amorphous solid. Further details of the synthesis may be found in Example 33 of the Von Nussbaum et al. patent.

Schrimer et al. provides an improved synthesis of Compound 1 as depicted in the schemes provided in U.S. Published Application No, 2018/0072685. The improved method is available in two variants, with method variant (A) furnishing Compound 1 in 8 steps (see Schemes 7, 2 and 3, of U.S. 2018/0072685) in more than 17% of theory overall yield without a chromatographic purification of intermediates. Method variant (B) (see Schemes 7, 4, 5 and 6, of U.S. 2018/0072685) furnishes Compound 1 in 9 steps, likewise without a chromatographic purification of intermediates, with the overall yield depending on the reaction management, as described in detail in U.S. 2018/0072685.

Compound 1 is a white to yellow solid, with a melting point of 232° C. It is considered neutral and does not readily form salts. Compound 1 is not hygroscopic under normal storage conditions, Compound 1 is practically insoluble in water, very slightly soluble in ethanol, and soluble in acetone.

Pharmaceutical Compositions

Compositions containing (4S)-4-[4-cyano-2-(methylsulfonyl)phenyl]-3,6-dimethyl-2-oxo-1-[3-(trifluoromethyl) phenyl]-1,2,3,4-tetrahydropyrimidine-5-carbonitrile (Compound 1) or a pharmaceutically acceptable salt, polymorph, solvate, or solvates of salts thereof as the active ingredient may be advantageously used to treat chronic liver diseases. While it is possible for Compound 1 or a pharmaceutically acceptable salt, polymorph, solvate, or solvates of salts thereof to be administered alone, it is preferable to present it as a formulation. The compositions, or dosage forms, may be administered or applied singly, or in combination with other agents, including one or more diluents, disintegrants, surfactants or lubricants. The formulations may also deliver Compound 1 to a patient in combination with another pharmaceutically active agent.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional pharmaceutically acceptable carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. Said compositions are prepared according to conventional mixing, granulating, or coating methods, respectively, and contain 0.1 to 75%, preferably 1 to 50%, of the active ingredient.

By "pharmaceutically acceptable" it is meant the carrier, diluent or excipient must be compatible with the other ingredients of the formulation and not deleterious to the recipient thereof, Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets, including, but not limited to, diluents, disintegrants, surfactants and lubricants. These excipients may be, for example, inert diluents, such as calcium carbonate, sodium carbonate, lactose, calcium phosphate or sodium phosphate; granulating and disintegrating agents, for example, cornstarch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. A tablet may be made by compressing or molding the active ingredient optionally with one or more pharmaceutically acceptable ingredients. Compressed tablets may be prepared by compressing, in a suitable machine, the active ingredient in a free-flowing form such as a powder or granules, optionally mixed with a binder, lubricant, inert diluent, surface active, or dispensing agent. Molded tablets may be made by molding, in a suitable machine, a mixture of the powdered active ingredient and a suitable carrier moistened with an inert liquid diluent. Tablets may be prepared as described in the Examples below or as described in PCT Application WO 2017/081044 (May et al.), which is incorporated herein in its entirety.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. In particular, a pharmaceutical composition of the present invention may comprise a liquid-filled capsule dosage form in which the active ingredient is in solution in certain combinations of liquid and semi-solid excipients.

Compositions for oral administration may also be formulated as aqueous suspensions containing the active ingredient in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Oral suspensions of Compound 1 may be prepared as described in PCT Application WO 2017/081044 (May et al.).

The active ingredient of the present invention may be administered in an oral immediate release (IR) formulation or a sustained release formulation. "Sustained release" refers to release of an active agent from a dosage form at a rate effective to achieve a therapeutic amount of the agent, or active metabolite thereof, in the systemic blood circulation over a prolonged period of time relative to that achieved by oral administration of a conventional formulation of the agent. Release of the agent occurs over an extended period of hours, for example, over a period of at least 6 hours, over a period of at least 8 hours, over a period of at least 12 hours, or over a period of at least 24 hours.

Compound 1 may be administered by intravenous (i.v.) infusion. Solutions of Compound 1 suitable for intravenous administration may be prepared as described in PCT Published Application No. WO 2017/081044 (May et al.).

Suitable topical formulations and dosage forms include ointments, creams, gels, lotions, pastes, and the like, as described in *Remington: The Science and Practice of Pharmacy* ($21^{st}$ Edition, University of the Sciences in Philadelphia, 2005). Ointments are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. Gels are semisolid, suspension-type systems. Single-phase gels contain organic macromolecules (polymers) distributed substantially uniformly throughout the carrier liquid, which is typically aqueous, but also, preferably, contain an alcohol such as ethanol or isopropanol and, optionally, an oil. In order to prepare a uniform gel, dispersing agents such as alcohol or glycerin can be added, or the gelling agent can be dispersed by trituration, mechanical mixing or stirring, or combinations thereof. Lotions are preparations to be applied to the skin surface without friction, and are typically liquid or semiliquid preparations in which solid particles, including the active agent, are present in a water or alcohol base. Lotions are usually suspensions of finely divided solids and will typically contain suspending agents to produce better dispersions as well as compounds useful for localizing and holding the active agent in contact with the skin. Pastes are semisolid dosage forms in which the active agent is suspended in a suitable base. Depending on the nature of the base, pastes are divided between fatty pastes or those made from single-phase aqueous gels.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. For those drugs having an unusually low rate of permeation through the skin or mucosal tissue, it may be desirable to include a permeation enhancer in the formulation. The formulation may also contain irritation-mitigating additives to minimize or eliminate the possibility of skin irritation or skin damage resulting from the drug, the enhancer, or other components of the dosage form. The formulations may also contain ether physiologically acceptable excipients or other minor additives, such as fragrances, dyes, emulsifiers, buffers, cooling agents (e.g. menthol), antibiotics, stabilizers or the like. In some instances, one component may serve more than one function.

The concentration of the active agent in a topical formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. The formulations will typically contain on the order of 0.1 wt % to 50 wt % active agent, preferably 0.1 wt % to 5 wt % active agent, optimally 5 wt % to 20 wt % active agent.

The pharmaceutical compositions of the present invention may be formulated as a depot formulation for administration via intramuscular or subcutaneous injection. Depot formulations are efficient, well-tolerated, sustained or delayed release compositions of the active ingredient that are therapeutically effective for a number of weeks, such as at least one week, at least two weeks, at least three weeks, at least four weeks, at least five weeks, or at least six weeks or more. In addition to the active agent, additional ingredients may be used in the depot formulations of the present invention including surfactants, solubilizers, emulsifiers, preservatives, isotonicity agents, dispersing agents, wetting agents, fillers, solvents, buffers, stabilizers, lubricants, and thickening agents. A combination of additional ingredients may also be used. The amount of the active ingredient in a depot formulation will depend upon the severity of the chronic liver disease being treated.

The compositions of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration. These examples of unit dosage forms is not intended to be limiting in any way, but merely to represent typical examples in the pharmacy arts of unit dosage forms.

The compositions of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

NAFLD and NASH

Non-alcoholic fatty liver disease (NAFLD) is, essentially, a condition in which fat builds up in the liver (steatosis). The term covers a progressive spectrum of diseases from simple steatosis to nonalcoholic steatohepatitis, fibrosis and cirrhosis. Nonalcoholic steatohepatitis (NASH) is defined as the presence of steatosis (hepatic lipid accumulation) coexisting with hepatic inflammation and hepatocellular injury (steatohepatitis). NASH is a more advanced form of NAFLD where liver injury has occurred, and simple benign steatosis can evolve into fibrosis and cirrhosis, leading to end-stage liver disease, including development of hepatocellular carcinoma (Staels, B., et al., *Hepatology*, 2013, 58:1941-1952).

NAFLD is the most common form of liver disease worldwide, with a prevalence of 15%-30% in Western populations and is caused by triglyceride accumulation within the liver. However, the prevalence increases to 58% in overweight populations and 98% in obese populations. More than a quarter of adults with NAFLD are presumed to have NASH based on elevated serum aminotransferase levels and an absence of other identifiable causes of liver injury. A definitive diagnosis of NASH is currently based on histologic evidence not only of fat accumulation (steatosis) in hepatocytes but also of liver-cell injury and death and accumulation of inflammatory cells. Because livers with NASH are more damaged than livers with isolated steatosis, NASH is more likely than isolated steatosis to lead to progressive liver fibrosis and eventual liver-related illness and death (Diehl, A. M. and Day, C., *N. Engl. J. Med.*, 2017, 377:2063-72).

Several studies have suggested that obesity is associated with chronic adipose tissue inflammation, and adipose tissue has been shown to be infiltrated by pro-inflammatory cells such as lymphocytes, mast cells, natural killer cells, and neutrophils in the early stages of obesity (Elgazar-Carmon, V., et al., *J. Lipid Research*, 2008, 49:1894-1903; Feuerer, M., et al., *Nature Medicine*. 2009, 15:930-939; Liu, J., et al., *Nature Medicine*, 2009, 17(8):940-946; Nishimura, S., et al., *Nature Medicine*, 2009, 15(8):914-921; Weisberg, S. P., et al., *J. Clin. Invest.*, 2003, 112:1796-1808; Winer, D. A., et al., *Nature Medicine*, 2011, 17(5):610-618; and Xu, J., et al., *J. Clin. Invest.*, 2003, 112:1821-1830). Adipose inflammation has also been linked to the development of insulin resistance (Ouchi, N., et al., *Nature Reviews Immunol.*, 2011, 11:85-97; Osbom, O. and Olefsky, J. M., *Nature Medicine*, 2012, 18(3):363-374; and Sun, S., t al., *Annul. Rev Nutr.*, 2012, 32:261-286). Insulin resistance may in turn independently contribute to the pro-inflammatory and pro-fibrotic state and lead to NASH/NAFLD. Neutrophils participate in the inflammation that characterizes obesity, and NE is critical for modulating neutrophil-mediated regulation of adipose tissue and liver inflammation. As an NE inhibitor, Compound 1 is expected to exhibit both insulin-sensitizer and anti-inflammatory properties useful in the treatment of NASH/NAFLD (Talukdar, S., Olefsky, J. M., et al., *Nature Medicine*, 2012, 18(9):1407-1412).

Mice treated with recombinant murine NE demonstrate glucose intolerance, while NE knockout mice (NEKO) fed a high-fat diet (HFD) had a protected phenotype compared to wild-type controls, that is, decreased weight gain, lower white adipose tissue and liver weights, higher glucose tolerance, lower fasting insulin concentrations, higher hepatic and adipose tissue insulin sensitivities, and decreased adipose and hepatic neutrophil infiltration (Talukdar, et al., 2012). In the same study, the treatment of HFD mice with NE inhibitor GW311616A also protected the normal phenotype, improved glucose tolerance, and demonstrated increased peripheral and hepatic insulin sensitivity in glucose clamp/tracer studies. Similarly, Mansuy-Aubert et al. found that NE null (Ela2$^{-/-}$) mice and A1AT transgenic mice were resistant to high-fat diet (HFD)-induced body weight gain, insulin resistance, inflammation, and fatty liver. NE inhibitor GW311616A reversed insulin resistance and body weight gain in HFD-fed mice (Mansuy-Aubert, V., t al., *Cell Metabolism*, 2013, 17:534-548).

Furthermore, the mechanism by which NE mediates insulin resistance has been elucidated. Hepatic neutrophil infiltration and resultant NE activity is elevated in mice fed a HFD (Talukdar, 2012), consistent with observations in livers of obese patients with NASH (Rensen, S., at al., *Am. J. Pathol.*, 2009, 175:1473-1482). More specifically, the presence of neutrophils in the portal inflammatory infiltrate correlates with human disease progression to NASH (Gadd, V. L., at al., *Hepatology*, 2014, 59(4):1393-1405). Consistent with this observation, the neutrophil to lymphocyte ratio has been proposed as a potential novel biomarker to predict NASH and advanced fibrosis in patients with NAFLD (Alkhouri, N., et al., *Liver International*, 2012, 32(2):297-302). Treatment of hepatocytes with NE leads to cellular insulin resistance. Extracellular NE has been shown to enter the intracellular space and mediate degradation of insulin receptor substrate 1 (Irs1) (Houghton, A. M., et al., *Nature Med.*, 2010, 16(2):219-223; Houghton, A. M., *Cell Cycle*, 2010, 9(9):1732-1737). In an insulin-response study, NEKO animals were shown to have higher measures of insulin-signaling, as evidenced by an increase in Akt phosphorylation compared to WT controls (Talukdar 2012). Conversely, administration of recombinant NE resulted in a decrease in basal and insulin-stimulated Irs1 and p-Akt signaling in mouse liver and adipose tissue, and in primary mouse and human hepatocytes, prevented the ability of insulin to inhibit glucagon-stimulated hepatocyte glucose output.

To date, no human clinical trials have proven the efficacy of any proposed treatments for NAFLD/NASH. However, a number of animal models have been developed that mimic these diseases. The strong association between obesity and NAFLD has spurred the development of various diet-induced obesity (DIO) rodent models that mimic the etiology and natural history of NASH. Different strains of mice show varying susceptibility to NASH when fed a high-fat, high-cholesterol (obesogenic) diet. The most common strain used is C57BL/6 mice, which show a high susceptibility to obesogenic diets. These mice are also prone to developing diet-induced hepatic necroinflammation and fibrosis as compared to commonly used BALB/c and C3H/HeN mice. See Hansen, H. H., et al. (*Drug Discovery Today*, 2017, 22(11): 1707-1718.)

Zang et al. have investigated the role of neutrophils and of NE inhibitor sivelestat in C57BL/6J ApoE$^{-/-}$ mice fed a high fat, high cholesterol diet (Zang, S. F., et al., *Cell Biochemistry Biophysics*, 2015, 73(2):479-487; Zang, S. F., et al., *Chinese J. Hepatology*, 2017, 25(5):371-376)). The same research group has studied the imbalance between neutrophil elastase and its natural inhibitor α1-antitrypsin (A1AT) and the histological progression of NAFLD in affected patients vs. normal patients. They found that an increased NE:A1AT ratio is closed associated with liver inflammation in patients with NASH (Zang, S. F., et al., *Clinical Exper. Pharm.* Physiology, 2016, 43(1):13-21).

Therapeutic Administration and Doses

The terms "administration of" or "administering a" Compound 1 should be understood to mean providing (4S)-4-[4-cyano-2-(methylsufonyl)phenyl]-3,6-dimethyl-2-oxo-1-[3-(trifluoromethyl)phenyl]-1,2,3,4-tetrahydropyrimidine-5-carbonitrile or a salt, solvate, a solvate of a salt, or a polymorph, to the individual in need of treatment in a form that can be introduced into that individual's body in a therapeutically useful form and a therapeutically effective amount, including, but not limited to, oral dosage forms, such as tablets, capsules, syrups, suspensions, and the like.

The terms "treat", "treating" and "treatment" of chronic liver disease all refer to reducing the frequency of symptoms or signs of chronic liver disease (including eliminating them entirely), avoiding the occurrence of chronic liver disease and/or reducing the severity of symptoms or signs of chronic liver disease. The term "chronic liver disease" includes, but is not limited to, non-alcoholic fatty liver disease (NAFLD) and non-alcoholic steatohepatitis (NASH).

The term "therapeutically effective amount" refers to a sufficient quantity of Compound 1, in a suitable composition, and in a suitable dosage form to treat the noted disease conditions. The "therapeutically effective amount" will vary depending on the compound, the severity of the condition causing the chronic liver disease, and the age, weight, etc., of the patient to be treated.

The present methods for treatment of chronic liver disease require administration of Compound 1, or a pharmaceutical composition containing Compound 1, or a salt, solvate, a solvate of a salt, or a polymorph, to a patient in need of such treatment. The compound and/or pharmaceutical compositions are preferably administered orally. Various delivery systems are known, (e.g., encapsulation in liposomes, microparticles, microcapsules, capsules, etc.) can be used to administer Compound 1 and/or composition. The compound and/or pharmaceutical compositions may be delivered via immediate release (IR) or sustained release dosage forms.

The amount of Compound 1, a pharmaceutically acceptable salt, polymorph, solvate, or solvates of salts thereof, that will be effective in the treatment of a chronic liver disease in a patient will depend on the specific nature of the disease, and can be determined by standard clinical techniques known in the art. In addition, in vitro or in vivo assays may optionally be employed to help identify optimal dosage ranges. The specific dose level for any particular individual will depend upon a variety of factors including the activity of the composition, the age, body weight, general physical and mental health, genetic factors, environmental influences, sex, diet, time of administration, route of administration, rate of excretion, and the severity of the condition being treated.

Preferably, the dosage forms are adapted to be administered to a patient three, two or one time a day. More preferably, a therapeutically effective amount is taken once per day. Alternatively, a dose may be taken every other day, every third day, every fourth day or once a week. Dosing may be provided alone or in combination with other drugs and may continue as long as required for effective treatment of chronic liver disease.

Compound 1 may be administered in combination with one or more additional therapeutic agents. In one embodiment, Compound 1 may be administered with other NE inhibitors. Such NE inhibitors include, but are not limited to, silevestat (ONO-5046; Elaspol®; Ono Pharmaceutical); endogenous serine protease inhibitors (SERPINs); alpha-1 antitrypsin (AAT); elafin (Tiprelestat; Proteo, Inc.); alpha-1 protease inhibitor (alpha-1 PI; Prolastin®, GrifolsUSA; Zemaira®, CLS Behring LLC; Aralast®, Baxter); MR-889 (midesteine): GW311616A (GlaxoWellcome); GW475151 (GlaxoWellcome); 1,2,5-thiadiazolidin-3-one (ICI 200,880): AX-9657; freselest (ONO-6818; Tocris Bioscience); avelestat (AZD9668; AstraZeneca); and BAY-678 (Tocris Bioscience).

In another embodiment, Compound 1 may be administered in combination with another therapeutic agent or agents that treat or ameliorate NAFLD or NASH via a mechanism other than inhibition of neutrophil elastase. Such therapeutic agents include, but are not limited to, Elafibranor® (GFT505; Genfit), a PPAR alpha and delta agonist; seladelpar (MBX-8025; Cymabay Therapeutics), a selective PPAR delta agonist; Regenerate® (Obeticholic Acid; Intercept Pharmaceuticals. Inc.), a farnesoid X receptor agonist; Aramachol™ (Galmed Pharmaceuticals), a stearoyl CoA desaturase-1 inhibitor; cenicriviroc (CVC; Allergan), a CCR2 and CCR5 chemokine inhibitor; eicosapentanoic acid (EPA-E, Mochida Pharmaceuticals), inhibition of ROS production; Emricasan (Conatus Pharmaceuticals), a caspase inhibitor; Crestor® (rosuvastatin; AstraZeneca); GR-MD-02 (Galectin Therapeutics), a galectin-3 inhibitor, GS-0976 (Gilead), an acetyl CoA carboxylase inhibitor; selonsertib (GS-4997; Gilead), an ASK1 inhibitor; GS-6624 (simtuzumab, Gilead), an inhibitor of LOXL2; GS-9674 (Gilead), a farnesoid X receptor agonist; LJN452 and LMB763 (Novartis), farnesoid X receptor agonists; Lipitore (atorvastatin. Pfizer), a lipid-lowering agent; MGL-3196 (Madrigal), a selective thyroid hormone receptor-beta agonist; BMS-986036 (Bristol Myers Squibb), a pegylated FGF21; NGM282 (NGM Biopharmaceuticals), a non-tumorigenic analog of human FGF19; Pravacol® (pravastatin, Bristol-Myers Squibb) a lipid-lowering agent; Procysbi® (cysteamine bitartrate, Horizon); TERN-101 (Tems Pharmaceuticals Inc.), a farnesoid X receptor (FXR) agonist; TERN-201 (Terns Pharmaceuticals Inc.), a semicarbazide-sensitive amine oxidase (SSAO) inhibitor; tipelukast (MN-001; MediciNova, Inc.), a leukotriene (LT) receptor antagonist; volixibat (SHP-626; Shire), an ileal sodium bile acid co-transporter inhibitor, and Xenical® (orlistat, Roche), a lipid-lowering agent.

Chronic liver diseases NAFLD and NASH often occur in patients suffering from diabetes. Thus, it may be particularly appropriate to administer Compound 1 in combination with drugs intended to treat or to ameliorate the effects of diabetes, where those drugs are other than insulin or its derivatives, particularly if those agents also show efficacy in the treatment of NAFLD or NASH. In one embodiment, appropriate anti-diabetes agents include, but are not limited to, liraglutide (ex., Victoza® from Novo Nordisk; Saxenda® from Novo Nordisk); dulaglutide (Trulicity®; Eli Lilly); acarbose (Precose®; Bayer); albiglutide (Tanzeum®; GlaxoSmithKline); alogliptin (Nesina®; Takeda); bromocriptine mesylate (Cycloset®; Salix Pharmaceuticals); canaglifozin (Invokana®, Janssen Pharmaceuticals); dapagliflozin (Farxiga®; AstraZeneca); empagliflozin (Jardiance®; Boehringer Ingeheim); ipragliflozin (Suglat®; Astellas Pharma); glimepiride (Amaryl; Sanofi-Aventis); glyburide (DiaBeta®; Sanofi-Adventis); luseogliflozin (Lusefit); Taisho Pharmaceutical); metformin; miglitol (Glyset®; Pfizer); probucol; repaglinide (Prandin®; Novo Nordisk); pioglitazone (Actos®); rosiglitazone (Avandia®); saxagliptin (Onglyza®; AstraZeneca); semaglutide (Ozempic®; Novo Nordisk); and sitagliptin (Januvia®; Merck).

Dosage ranges of Compound 1 for oral administration may be stated in terms of total amount of drug administered over a certain frequency of administration. A certain amount of active ingredient may be given one or more times a day as appropriate according to the factors described above. For example, doses may be taken once a day, twice a day, three times a day, four times a day, or more. Suitable dosages range from 0.1 mg to 100 mg, and preferably, from 1 mg to 20 mg, one or more times a day. Suitable dosages are typically 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, 30 mg, 40 mg, 50 mg, or 100 mg one or more times per day. Preferably, a dose of 1 mg, 2 mg, 5 mg, 10 mg or 20 mg is administered once per day.

Alternatively, dosage ranges of Compound 1 for oral administration may be stated in terms of a weight-dependent dose. Suitable does are generally 0.001 mg to 1 mg of drug per kilogram body weight (mg/kg), one or more times a day. Suitable weight-dependent dosages are typically 0.001 mg/kg, 0.0015 mg/kg, 0.002 mg/kg, 0.0025 mg/kg, 0.005 mg/kg, 0.0075 mg/kg, 0.01 mg/kg, 0.02 mg/kg, 0.025 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.3 mg/kg, 0.4 mg/kg, 0.5 mg/kg or 1 mg/kg, one or more times per day, and preferably 0.01 mg/kg, 0.02 mg/kg, 0.05 mg/kg, 0.1 mg/kg, or 0.2 mg/kg, once per day. Dosage ranges may be readily determined by methods known to the skilled artisan. The amount of active ingredient that may be, for instance, combined with carrier materials to produce a single dosage form will vary depending upon the patient treated and the particular mode of administration.

Determination of Therapeutic Effectiveness

The effectiveness of the methods and compositions of the present invention can be tested in experimental animal models of chronic liver disease known to those skilled in the art. In particular, the diet-induced obesity (DIO) rodent models of NAFLD and NASH described above are appropriate. These models typically utilize C57BL/6 mice, which show a high susceptibility to obesogenic diets. These mice are also prone to developing diet-induced hepatic necroinflammation and fibrosis, similar to the same conditions in humans. See Hansen, H. H., et al. (*Drug Discovery Today*, 2017, 22(11):1707-1718.)

For example, in one model, DIO mice are dosed with Compound 1 via oral gavage daily (QD or BID). Matched control DIO mice receive vehicle only. The animals are observed for a period of time ranging from weeks to months, including monitoring of their body weight and other parameters. The mice are humanely sacrificed, terminal blood samples are collected, and the livers and other organs examined for differences between the two groups of mice. Many parameters may be compared, including liver enzymes, plasma lipids, expression of various marker genes, markers of inflammation, and NAFLD Active Score including degree of fibrosis formation.

The efficacy of the methods and compositions of the present invention in the treatment of chronic liver disease can also be evaluated in human clinical trials conducted under appropriate standards and ethical guidelines as set forth by the U.S. Food and Drug Administration (FDA) and other international agencies. After the general safety and pharmacokinetics of a drug is determined in Phase 1 clinical trials typically conducted in healthy volunteers, Phase 2 trials assessing the safety and efficacy of the drug in patients with the condition to be treated or target disease are conducted. Typically, such trials are double-blinded and controlled, and may be dose-ranging. Phase 3 studies gather more information about safety and attempt to prove effectiveness by studying the target population at specific dosages and, optionally, by using the drug in combination with other drugs.

The following examples are offered by way of illustration and not by way of limitation.

EXAMPLES

Example 1. Preparation of Tablets

Compound 1, (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile, may be formulated as a tablet for oral use. Manufacture of these tablets utilizes standard pharmaceutical process technologies. All of the inactive pharmaceutical ingredients in the examples below comply with requirements of United States Pharmacopeia (USP), The National Formulary (NF), the European Pharmacopeia (Ph. Eur.) and/or the Japanese Pharmacopeia (Ph. Jap.) as noted and are tested and released according to the monograph for each ingredient specified in the indicated standard. Batch sizes vary according to the amounts needed for a particular clinical purpose. The two examples below demonstrate the qualitative/quantitative composition of exemplary dosages and are for illustrative purposes. It is understood that additional dosage sizes and batch amounts are contemplated by the present invention.

Example 1a. Preparation of 0.5 mg Tablets

The batch composition for 0.5 mg oral tablets is shown in Table 1.

TABLE 1

| Composition | Reference to Quality Standard | Percent of Blend | Amount (g) |
|---|---|---|---|
| Intragranular | | | |
| Micronized Compound 1 | In house | 0.588% | 17.50 |
| Hydroxypropylcellulose 5 cP | Ph. Eur., USP/NF | 2.00% | 59.50 |
| Croscarmellose sodium | Ph. Eur., USP/NF, Ph. Jap. | 4.00% | 119.0 |
| Lactose monohydrate | Ph. Eur., NF | 92.41% | 2,749.3 |
| Purified water in bulk[1] | N.A. | N.A. | N.A. |
| Extragranular | | | |
| Magnesium stearate | Ph. Eur., Ph. Jap. | 1.00% | 29.8 |
| Film Coating | | | |
| White Lacquer | Opadry ™ white[2] | N.A. | 122.50 |
| Purified water in bulk[1] | N.A. | N.A. | N.A. |
| Total | | | 3,097.6 |

[1]Purified water in bulk is used as solvent that is removed during the manufacturing process.
[2]Contains: Hypromellose 15 cP, Ph. Eur., NF, Ph. Jap.; Macrogol, Ph. Eur., USP, Ph. Jap.; Titanium dioxide, Ph. Eur., Directive 95/45/EC, USP, Ph. Jap.

Using the amounts specified in Table 1, micronized Compound 1, sodium croscarmellose and lactose monohydrate and are mixed in a fluidized bed granulator. A solution of hydroxypropylcellulose in water is added as the granulation liquid. After granulation, drying, milling and screening, extra-granular magnesium stearate is added. The final blend is compressed into tablets, which are tested for uniformity of mass, thickness and resistance to crushing. The tablets are coated with a solution of Opadry™ in water. The coated tablets are visually inspected for defects. Tablets with visible coating defects are rejected.

Example 1b. Preparation of 1 and 5 mg Tablets

The batch composition for 1 mg and 5 mg oral tablets are shown in Tables 2 and 3, respectively.

TABLE 2

| Component | Reference to Quality Standard | Percent of Blend | Amount (g) |
|---|---|---|---|
| Intra-granular | | | |
| Micronized Compound 1 | In-house | 1.19% | 40.4 |
| Lactose monohydrate | USP/NF, Ph. Eur., Ph. Jap | 45.91% | 1,560.8 |
| Hydroxypropylcellulose | USP/NF, Ph. Eur., Ph. Jap | 2.00% | 68.0 |
| Croscarmellose sodium | Ph. Eur., NF, Ph. Jap. | 4.00% | 136.0 |
| Purified water in bulk[1] | N.A. | N.A. | N.A. |
| Extra-granular | | | |
| Microcrystalline cellulose | NF, Ph. Eur., Ph. Jap. | 45.91% | 1,560.8 |
| Magnesium stearate | NF, BP/Ph. Eur., Ph. Jap. | 1.00% | 34.0 |
| Film Coating | | | |
| White lacquer | Opadry ™ II white[2] | N.A. | 140.0 |
| Purified water in bulk[1] | N.A. | N.A. | N.A. |
| Total | | | 3,400.0 |

[1]Purified water in bulk is used as solvent that is removed during the manufacturing process.
[2]Contains: Polyvinyl alcohol, Ph. Eur., USP, FCC, Ph. Jap.; Macrogol, Ph. Eur., USP, FCC, JECFA, Ph. Jap.; Titanium dioxide, Ph. Eur., USP, FCC, Ph. Jap., Chp, GB; Talc, USP, FCC, Ph. Eur., Ph. Jap., JECFA.

TABLE 3

| Component | Reference to Quality Standard | Percent of Blend | Amount (g) |
|---|---|---|---|
| Intra-granular | | | |
| Micronized Compound 1 | in-house | 5.96% | 60.8 |
| Lactose monohydrate | USP/NF, Ph. Eur., Ph. Jap | 43.52% | 443.9 |
| Hydroxypropylcellulose | USP/NF, Ph. Eur., Ph. Jap | 2.00% | 20.4 |
| Croscarmellose sodium | Ph. Eur., NF, Ph. Jap. | 4.00% | 40.8 |
| Purified water in bulk[1] | N.A. | N.A. | N.A. |
| Extra-granular | | | |
| Microcrystalline cellulose | NF, Ph. Eur., Ph. Jap. | 43.52% | 443.9 |
| Magnesium stearate | NF, BP/Ph. Eur., Ph. Jap. | 1.00% | 10.2 |
| Film Coating | | | |
| White lacquer | Opadry ™ II white[2] | N.A. | 42.0 |
| Purified water in bulk[1] | N.A. | N.A. | N.A. |
| Total | | | 1,062.0 |

[1]Purified water in bulk is used as solvent that is removed during the manufacturing process.
[2]Contains: Polyvinyl alcohol, Ph. Eur., USP, FCC, Ph. Jap.; Macrogol, Ph. Eur., USP, FCC, JECFA, Ph. Jap.; Titanium dioxide, Ph. Eur., USP, FCC, Ph. Jap., Chp, GB; Talc, USP, FCC, Ph. Eur., Ph. Jap., JECFA.

Using the amounts specified in Tables 2 and 3, micronized Compound 1, sodium croscarmellose and lactose monohydrate and are mixed in a high shear granulator. A solution of hydroxypropylcellulose in water is added as the granulation liquid. After granulation, drying, milling and screening, extra-granular microcrystalline cellulose and magnesium stearate are added, with blend uniformity being tested prior to addition of the magnesium stearate. The final blend is compressed into tablets, which are tested for uniformity of mass, thickness and resistance to crushing. The tablets are coated with a solution of Opadry™ II in water. The coated tablets are visually inspected for defects. Tablets with visible coating defects are rejected.

Example 2. Effect of Compound 1 on Glucose Tolerance in DIO Mice

Methods.

Male DIO (diet-induced obesity) mice (C57BLJ6NTac DIO MPF, n=35) were purchased from Taconic Biosciences (Rensselaer, N.Y.). DIO mice were prepared by feeding male C57BL16 mice a high fat diet (HFD, D12492; Research Diets, Inc., New Brunswick, N.J.) from 6-16 weeks of age. A twelve-hour light cycle was maintained throughout study duration. Room temperature was monitored daily and maintained at 22-25° C. DIO mice were housed individually and maintained on the HFD during a 7-day facility acclimation period and throughout the study period. All mice were administered vehicle (5% DMSO/3% ethanol/92% peanut oil) once daily during the acclimation period.

Following 7 days of facility acclimation, DIO mice were randomized into 4 groups of 8 based on body weight and fasted (6 hours) blood glucose for assignment to receive vehicle, rosiglitazone 30 mg/kg/day, or Compound 1 at 3.0 mg/kg/day or 15 mg/kg/day. Compounds were administered once daily in the morning by oral gavage for 6 weeks. Dose volume was maintained at 5 ml/kg throughout the study. Compound 1 was provided in powder form and was formulated fresh weekly. Rosiglitazone (lot # FOJ407) was provided by CBIN; rosiglitazone was also formulated fresh weekly. Rosiglitazone (Avandia®) is an anti-diabetic drug in the thiazolidinedione class.

Whole blood was obtained weekly from fed animals by tail clip for measurement of non-fasted blood glucose (StatStrip; Nova Biomedical, Waltham, Mass.) on day 7, day 14, day 21 and day 35 after first dosing. Body weight was recorded prior to glucose measurement at baseline and weekly thereafter. Oral glucose tolerance tests were performed in fasted mice at baseline (day −1), day 28 and day 42 thereafter. Rosiglitazone or Compound 1 was administered 1 hour into the fasting period. At the end of the 6-hour fasting period, mice were challenged with glucose (2 g/kg, 10 ml/kg, by oral gavage). Blood samples were obtained by tail clip at 0, 20, 40, 60, 90 and 120 minutes post-glucose load for assessment of blood glucose by StatStrip. Serum insulin was measured from time 0 blood samples of OGTT using the Mouse/Rat Insulin Kit (MSD #K152BZC; Meso Scale Diagnostics, Rockville, Md.).

Animals were terminated using $CO_2$ inhalation and induction of pneumothorax. Four mice from each treatment group were sacrificed at 0.5 hr post dose and four were sacrificed at 4 hours post dose. Terminal blood samples (K2EDTA) were obtained by cardiac puncture and processed to plasma for determination of compound concentrations. Organ weights (liver, epididymal fat) were recorded.

Results.

All data are represented as group mean±SEM. Data were analyzed using JMP (SAS software). All normalizations were calculated using terminal body weight. All assigned animals completed the study. One animal receiving Compound 1 at 3 mg/kg was identified as an outlier for several measured parameters (Mahalanobis, $T^2$) and was eliminated from all analysis. The sum of the trapezoidal areas between the 0, 30, 60, 90 and 120-minute time points corresponding to each animal were summed to obtain the area under the curve (AUC) for glucose from OGTT data. Treatment effects compared to vehicle were determined using Oneway ANOVA (*, p<0.05) followed by Dunnett's test where appropriate.

Body weight Body weight in 18 week old DIO mice averaged 42.5±0.4 g and there were no significant differences compared to vehicle for any treatment group at baseline (42.2±0.7, 42.8±1.0, 42.8±1.1 and 42.8±1.0, for vehicle, rosiglitazone, and Compound 1 at 3 and 15 mg/kg, respectively).

Figure 2:
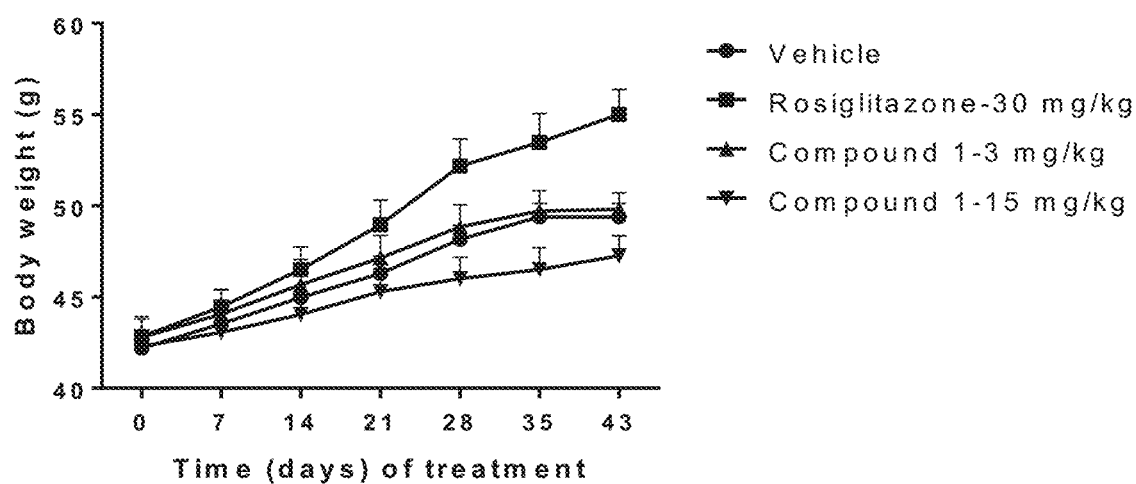
FIG. 2 shows the change in body weight of diet-induced obesity (DIO) mice during 6 weeks of treatment with rosiglitazone, 3 mg/kg Compound 1, 15 mg/kg Compound 1, or vehicle: A) body weight in grams plotted against days of treatment for the four treatment groups; B) graphical depiction of the terminal body weight for the four treatment groups; C) body weight (percentage) plotted against days of treatment for the four treatment groups; D) graphical depiction of percentage body weight growth rate for the four treatment groups.
Figure 2:
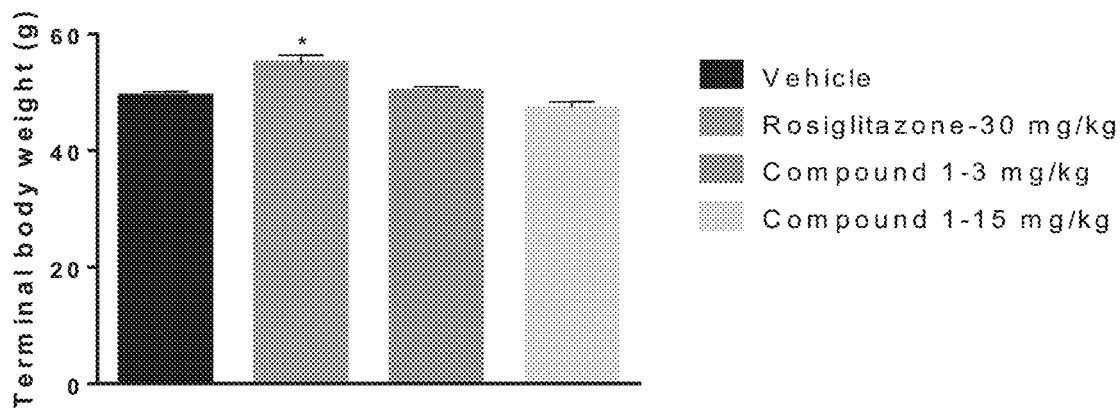
Figure 2:
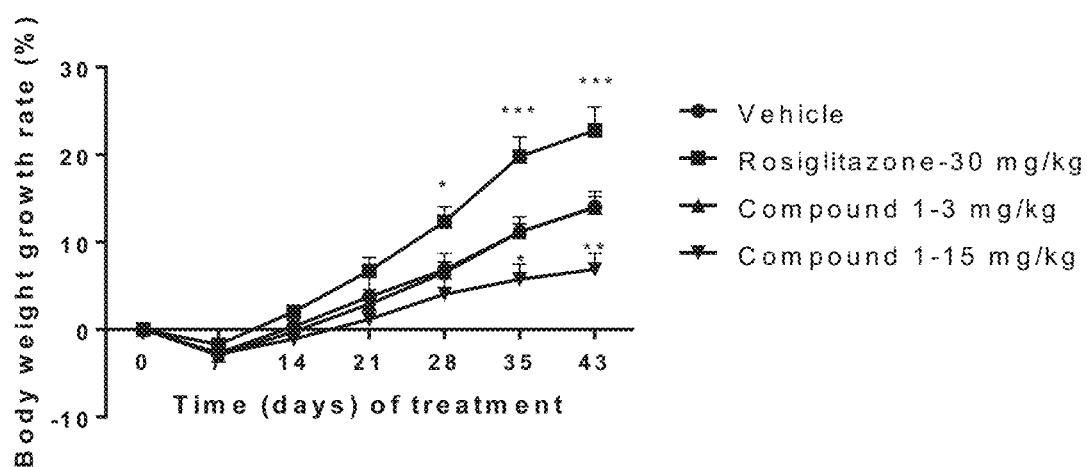
Figure 2:
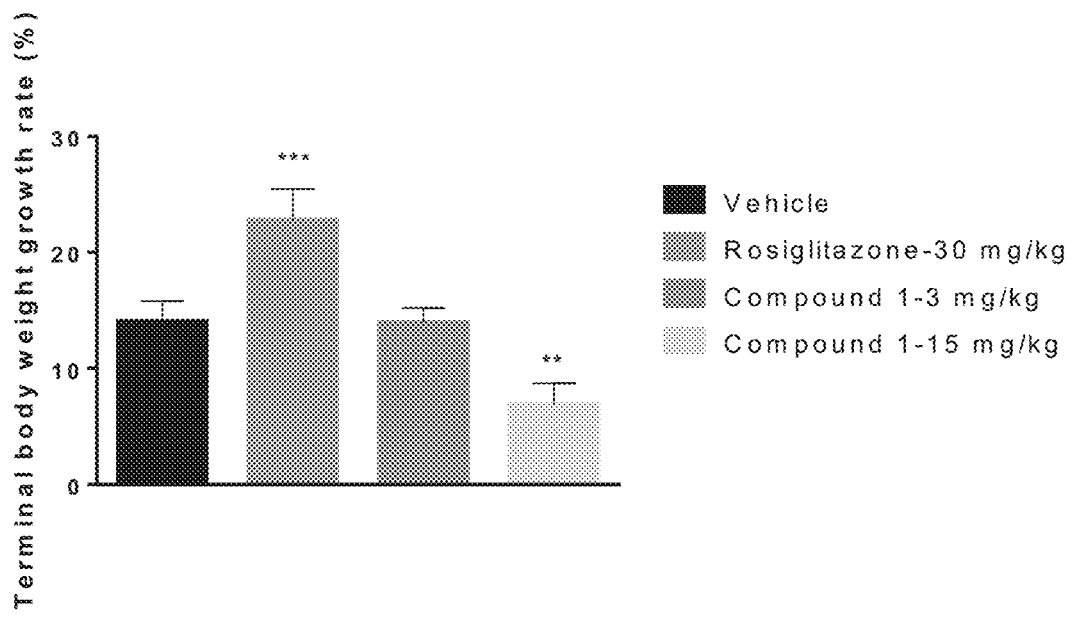

Body weight increased compared to baseline in all treatment groups during the 6 week study as shown in FIG. 2A Mice administered rosiglitazone were significantly heavier following 6 weeks of treatment than vehicle treated animals (49.4±0.7 vs. 55.0±1.4 g). Although no statistically significant effects of Compound 1 on body weight were noted compared to vehicle (49.4±0.7, 49.8±0.9 and 47.3±1.1 g for vehicle and Compound 1 at 3 mg/kg and 15 mg/kg, respectively) at the end of the study as shown in FIG. 2B, Compound 1 at 15 mg/kg showed a significantly lower growth rate of body weight comparing to vehicle (14±1.8% and 6.9±1.8% for vehicle and Compound 1, respectively). See FIGS. 2C and 2D.

Blood Glucose.

Blood glucose (fasted) in 18 week old mice averaged 163.1±3.9 mg/dL and there were no significant differences compared to vehicle at study start (163.0±12.7, 164.0±4.0, 160.3±5.7 and 164.6±7.3 mg/dL for vehicle, rosiglitazone and Compound 1 at 3 and 15 mg/kg, respectively). Fasted blood glucose decreased compared to baseline values in all treatment groups, including vehicle treated mice, as the study progressed. Fasting glucose in rosiglitazone treated mice was decreased compared to baseline by 23% (164.0±4 to 125.8±4.8 mg/dL) after 6 weeks of treatment; however, fed glucose on day 35 was not significantly different compared to vehicle (134.5±6.9 vs. 125.5±4.5 mg/dL). Fasting glucose was decreased from baseline in Compound 1 treated mice by 11% for the 15 mg/kg dose following 6 weeks of treatment. Similarly, fed glucose on day 35 was not significantly different compared to vehicle for any Compound 1 treated group (134.5±6.9, 128.3±3.4 and 134.9±4.7 mg/dL for vehicle and Compound 1 at 3 and 15 mg/kg, respectively).

OGTT.

Figure 3:
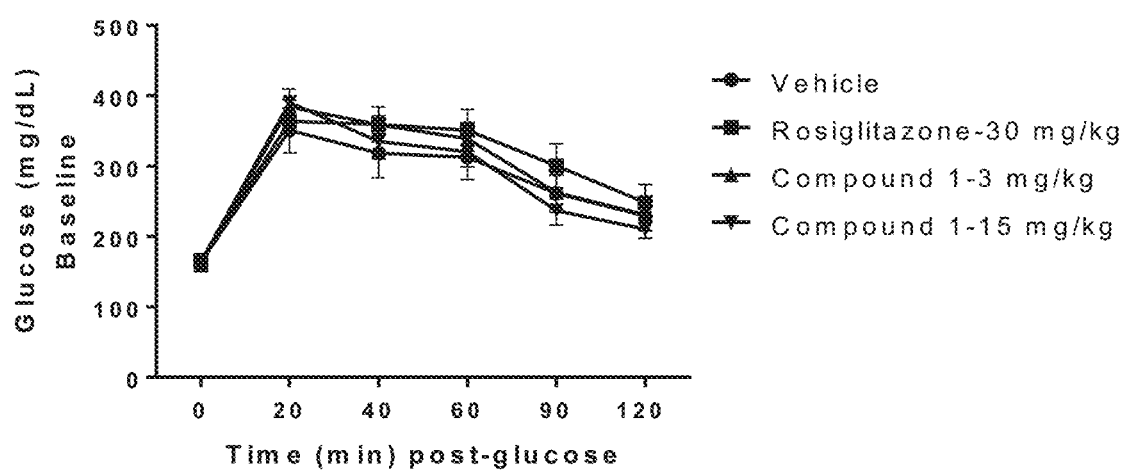
FIG. 3 shows the glucose disposal curves for DIO mice during 6 weeks of treatment with rosiglitazone, 3 mg/kg Compound 1, 15 mg/kg Compound 1, or vehicle: A) glucose disposal curves following an oral dose of glucose challenge determined on the day before treatment day (Day −1) for the four treatment groups; B) glucose disposal curves after four weeks of treatment (Day 28) for the four treatment groups; C) glucose disposal curves after six weeks of treatment (Day 42) for the four treatment groups; D) graphical depiction of the incremental glucose AUC before (Day −1) and after (Day 28 and Day 42) treatment for the four treatment groups.
Figure 3:
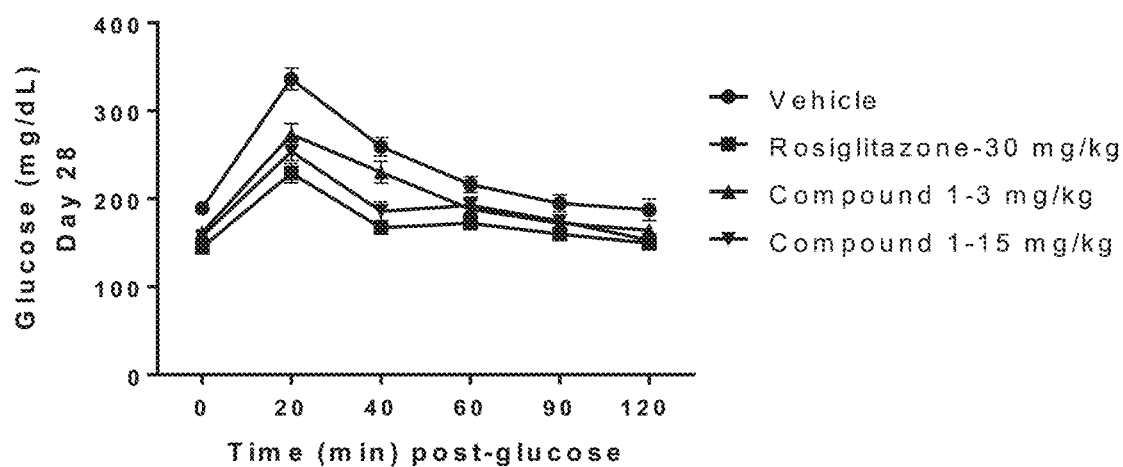
Figure 3:
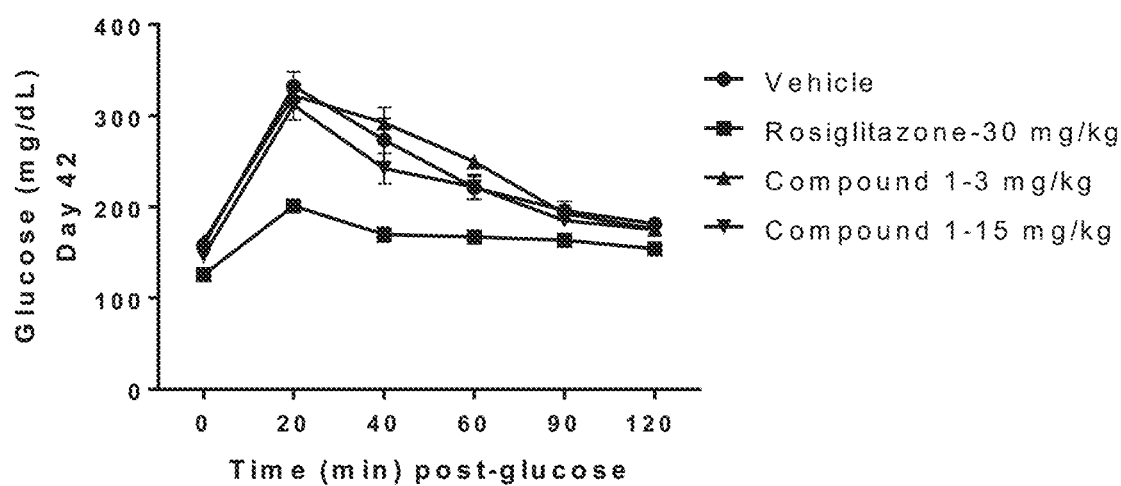
Figure 3:
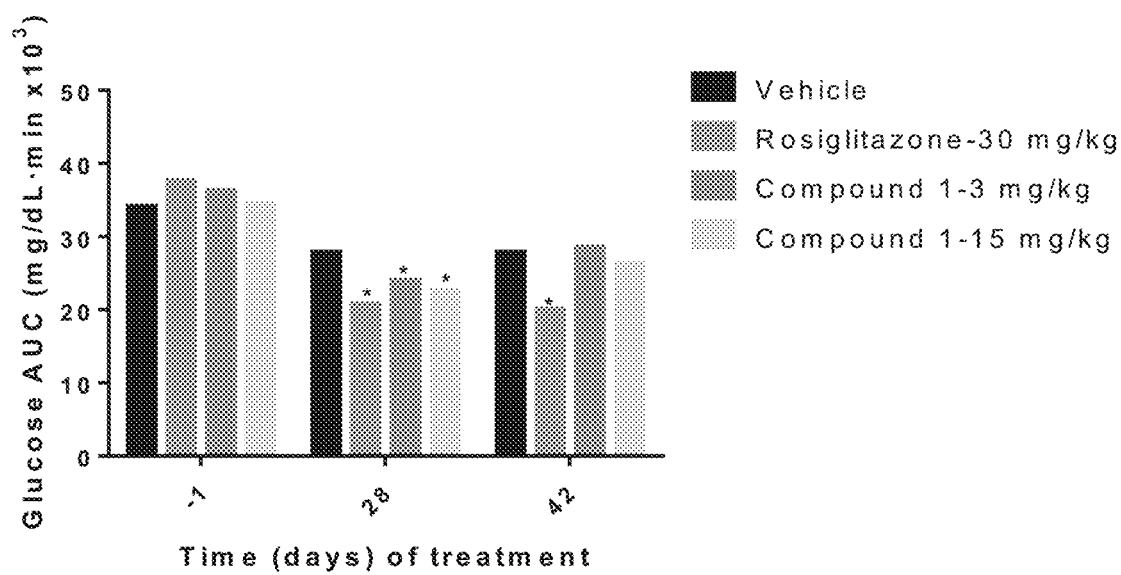

The glucose disposal curves for vehicle, rosiglitazone and Compound 1 treated mice are superimposable at baseline as shown in FIG. 3A such that no significant differences in the glucose AUC among groups were noted (34.12±3.3, 37.6±2.6, 36.3±2.0, and 34.4±2.2 mg/dL·min×10³ for vehicle, rosiglitazone and Compound 1 at 3 and 15 mg/kg, respectively) as shown in FIG. 3D. Following 28 days of treatment, changes in the glucose disposal curves compared to vehicle are apparent for rosiglitazone and both Compound 1 treated groups as shown in FIG. 3B; the glucose AUC on day 28 was significantly lower compared to vehicle for rosiglitazone and both Compound 1 treated groups, (27.9±1.1, 20.7±0.4, 24.0±0.9 and 22.7±0.7 mg/dL·min×10³ for vehicle, rosiglitazone and Compound 1 at 3 and 15 mg/kg, respectively) as shown in FIG. 3D. While the effect of rosiglitazone on the glucose disposal curve remains apparent on day 42, the response of Compound 1 appears transient as those curves are approaching vehicle at this time point as shown in FIG. 3C. Indeed, the glucose AUC for rosiglitazone remained significantly lower compared to vehicle (27.8±1.2 vs. 20.1±0.5 mg/dL/min×10³) while the significance of the Compound 1 treatment compared to vehicle was lost (27.8±1.2, 28.6±0.7 and 26.3±1.1 mg/dL/min×10³ for vehicle and Compound 1 at 3 and 15 mg/kg/day, respectively) as shown in FIG. 3D.

The glucose AUC on day 42 represented a decrease compared to baseline values for rosiglitazone (44.9±3.9%), Compound 1 3 mg/kg (20.0±4.5%) and Compound 1 15 mg/kg (−21.9±5.0%). The decrease in AUC from baseline in vehicle treated animals was 12.6±10.3%. This effect was significant compared to vehicle for rosiglitazone treated animals only.

Fasted Serum Insulin.

Figure 4:
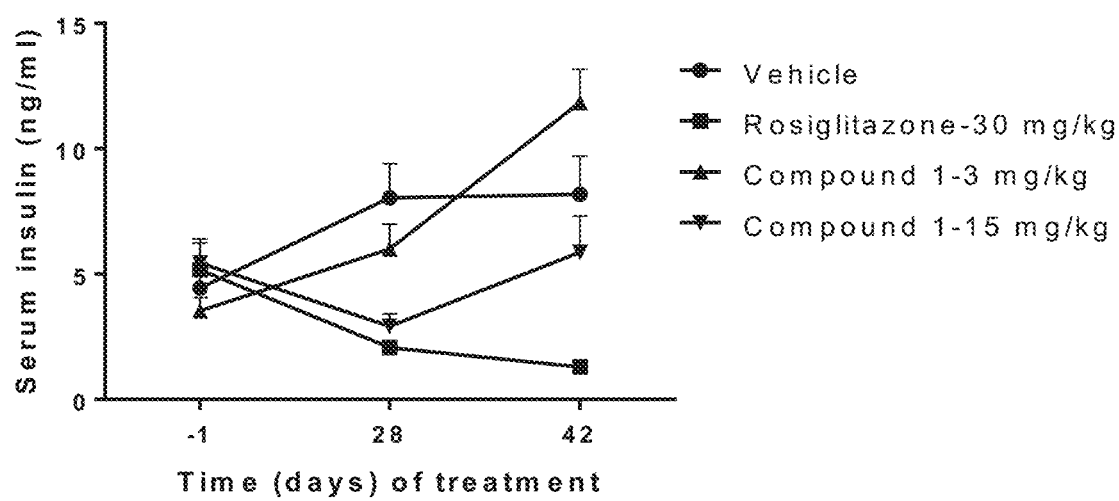
FIG. 4 shows the changes in fasted serum insulin levels for DIO mice during 6 weeks of treatment with rosiglitazone, 3 mg/kg Compound 1, 15 mg/kg Compound 1, or vehicle: A) serum insulin (ng/ml) plotted against days of treatment for the four treatment groups; B) graphical depiction of the fasted serum insulin levels for the four treatment groups at the end of the study.
Figure 4:
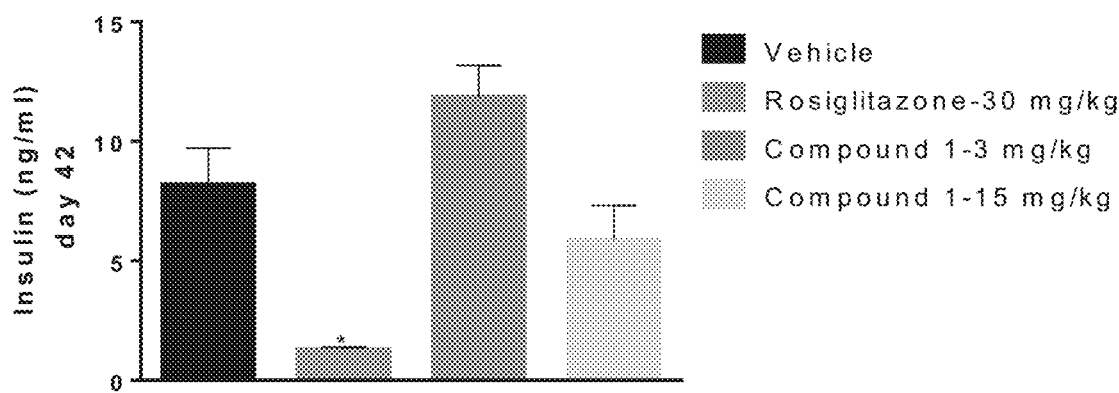

Fasted serum insulin averaged 4.7±0.4 ng/ml in 18 week old DIO mice at baseline; no differences in fasting insulin were noted among treatment groups at baseline (4.44±0.8, 5.2±1.1, 3.5±0.5 and 5.4±1.0 ng/ml for vehicle, rosiglitazone, and Compound 1 at 3 and 15 mg/kg, respectively) as shown in FIG. 4A. On day 42, fasted insulin levels were significantly lower compared to vehicle in mice administered rosiglitazone (8.2±1.5 vs. 1.3±0.1 ng/ml). Insulin levels were higher compared to vehicle for the low dose of Compound 1 (8.2±1.5 vs. 11.8±1.3 ng/ml) and lower compared to vehicle in animals treated with the higher dose of Compound 1 (8.2±1.5 vs. 5.9±1.5 ng/ml), but these effects were not significant compared to vehicle as shown in FIG. 4B.

Organ Weights.

Figure 5:
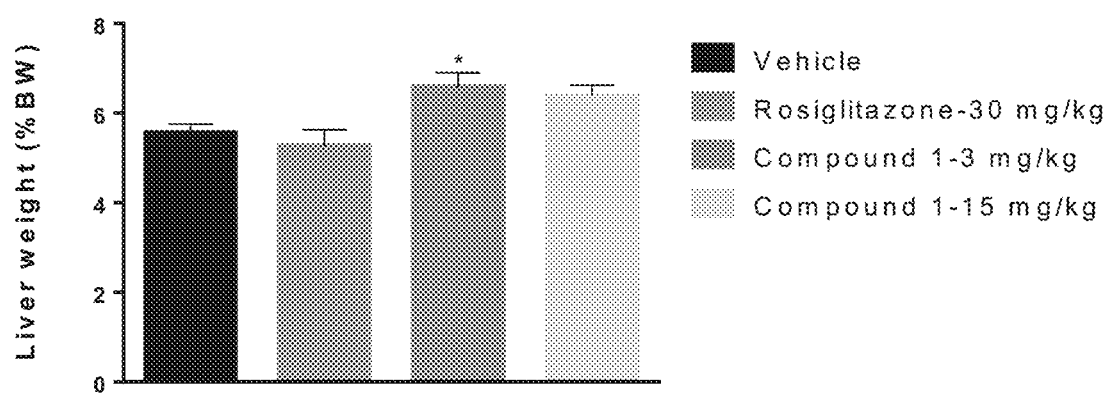
FIG. 5 shows a comparison of terminal liver and epididymal fat weights for DIO mice after 6 weeks of treatment with rosiglitazone, 3 mg/kg Compound 1, 15 mg/kg Compound 1, or vehicle: A) graphical depiction of the terminal liver weights expressed as a percentage of body weight for the four treatment groups; B) graphical depiction of the terminal epididymal fat weights expressed as a percentage of body weight for the four treatment groups.
Figure 5:
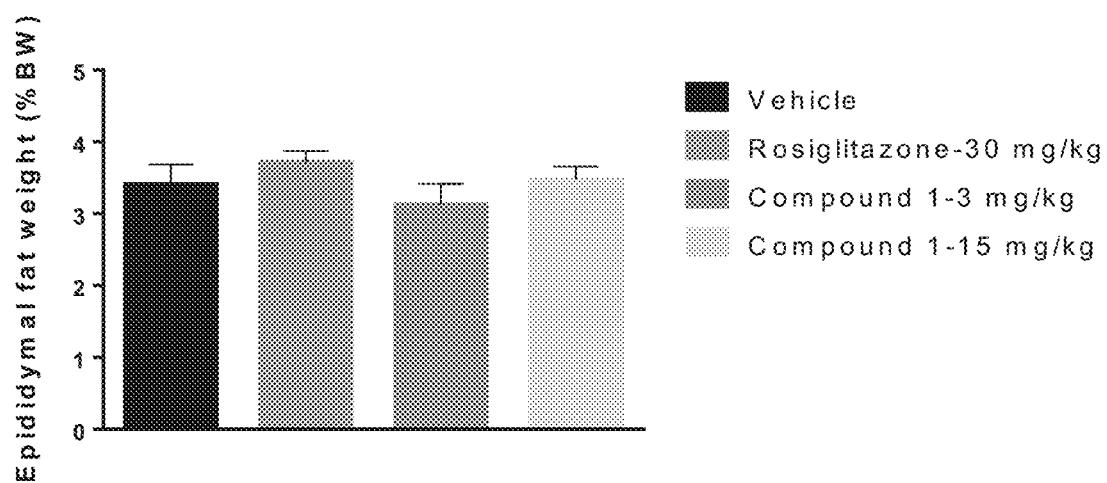

Liver weight (% body weight) was significantly higher compared to vehicle in mice administered Compound 1 at 3 mg/kg (5.6±0.2 vs. 6.8±0.3%). No other significant effects compared to vehicle on liver weight were noted (5.6±0.2, 5.0±0.2 and 6.4±0.2% for vehicle, rosiglitazone and Compound 1 at 15 mg/kg, respectively) as shown in FIG. 5A. No significant effects on epididymal fat weight were noted compared to vehicle (3.4±0.3, 3.7±0.2, 3.1±0.3 and 3.5±0.2% for vehicle, rosiglitazone and Compound 1 at 3 and 15 mg/kg, respectively) as shown in FIG. 5B.

Summary.

Based on clinical observations, Compound 1 (3-15 mg/kg/day) was generally well tolerated. After 6 weeks of treatment, animals administered rosiglitazone were heavier, had lower insulin levels and improvements in glucose disposal compared to vehicle treated mice, consistent with its known effects on body weight gain and insulin sensitization. While fasting blood glucose was reduced by rosiglitazone and 15 mg/kg Compound 1 throughout the study period, the fed blood glucose showed no significant difference in all groups. Compound 1 reduced body weight gain at the high dose and transient improvements in glucose handling and disposal were noted following administration of Compound 1 at 3 and 15 mg/kg.

Example 3. Effect of Compound 1 in the DIO Mouse Model of Obesity

Methods.

Male DIO mice (C57BL/6NTac DIO MPF, n=24) were purchased from Taconic Biosciences (Rensselaer. N.Y.). DIO mice were prepared at Taconic by feeding male C57BL/6 mice a high fat diet (HFD, Research Diets D12492) from 6 weeks of age. They arrived at the research facility at the age of 17 weeks and were continued on HFD until the end of study. A twelve-hour light cycle was maintained throughout the study duration from 6 am through 6 pm. Room temperature was monitored daily and maintained at 22-25° C. DIO mice were housed individually and maintained on the HFD during a 7-day facility acclimation period and throughout the study period. All mice were administered vehicle (5% DMSO/3% ethanol/92% peanut oil) once daily during the acclimation period.

Following 7 days of facility acclimation, DIO mice were randomized into 3 groups of 8 based on body weight and fasted (6 hours) blood glucose for assignment to receive vehicle, Compound 1 at 15 mg/kg or 30 mg/kg. Compounds were administered twice daily in the morning (6 am to 8 am) and at least 8 hours later dosing by oral gavage for 4 weeks as shown in Table 4. Dose volume was maintained at 5 ml/kg throughout the study. Compound 1 was provided in powder form and was formulated fresh on Monday, Wednesday and Friday with fresh vehicle solution each week.

TABLE 4

| Group # | Treatment | No. of Animals | Dose Level (mg/kg) | Dose Conc. (mg/ml) | Dose Volume (ml/kg) | Frequency | Route of Admin. |
| --- | --- | --- | --- | --- | --- | --- | --- |
| 1 | Vehicle | 8 | 0 | 0 | 5 | BID | PO |
| 2 | Compound 1 | 8 | 15 | 3 | 5 | BID | PO |
| 3 | Compound 1 | 8 | 30 | 6 | 5 | BID | PO |

Whole blood was obtained weekly from fed animals by tail clip for measurement of blood glucose (StatStrip) on day 7, day 14, and day 21 just before the first morning dosing. Body weight was recorded prior to glucose measurement at baseline and weekly thereafter.

Oral glucose tolerance tests (OGTTs) were performed in fasted (0600-1200) mice at baseline (day −1) and day 28. Compound 1 was administered 1 hour into the fasting period at around 7 am. At the end of the 6-hour fasting period, mice were challenged with glucose (2 g/kg, 10 ml/kg, by oral gavage) and blood samples were obtained by tail clip at 0, 20, 40, 60, 90 and 120 minutes post-glucose load for assessment of blood glucose by StatStrip. Serum insulin was measured from 6 h fasted blood samples on day −1 and day 29 using the mouse/Rat Insulin Kit (MSD #K152BZC).

Animals were terminated using $CO_2$ inhalation and induction of pneumothorax. All animals were sacrificed at 4 hours post dose for determination of compound concentrations. Terminal blood samples (K2EDTA) were obtained by cardiac puncture and processed to plasma.

Results.

All data are represented as group mean±SEM. Data were analyzed using Prism 7.0 (Graphpad software). All normalizations were calculated using terminal body weight. All assigned animals completed the study. The sum of the trapezoidal areas between the 0, 20, 40, 60, 90 and 120-minute time points corresponding to each animal were summed to obtain the area under the curve (AUC) for glucose from OGTT data. Treatment effects compared to vehicle were determined using Oneway ANOVA (*, $p<0.05$; *, $P<0.01$) followed by Dunnett's test where appropriate.

Body weight.

Figure 6:
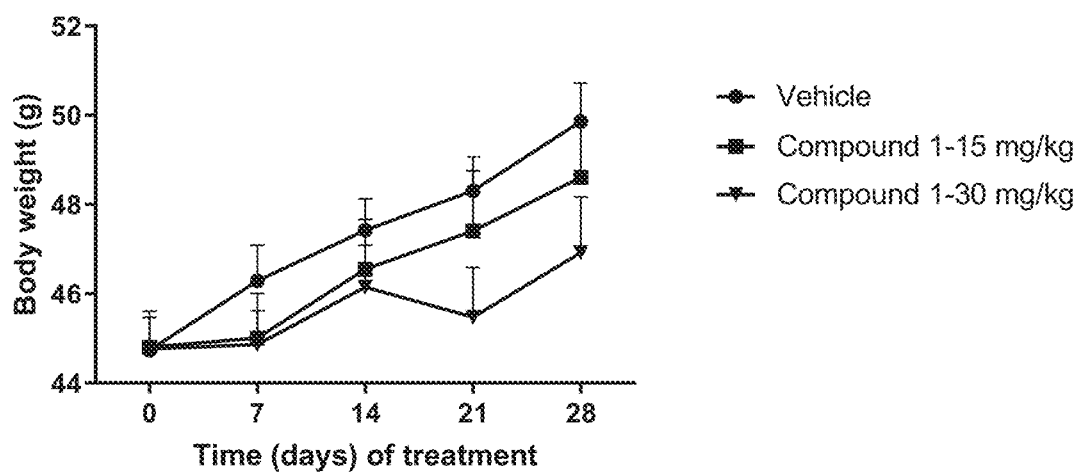
FIG. 6 shows the change in body weight of DIO mice during 4 weeks of treatment with 15 mg/kg Compound 1, 30 mg/kg Compound 1, or vehicle: A) body weight in grams plotted against days of treatment for the three treatment groups; B) body weight change (percentage) plotted against days of treatment for the three treatment groups.
Figure 6:
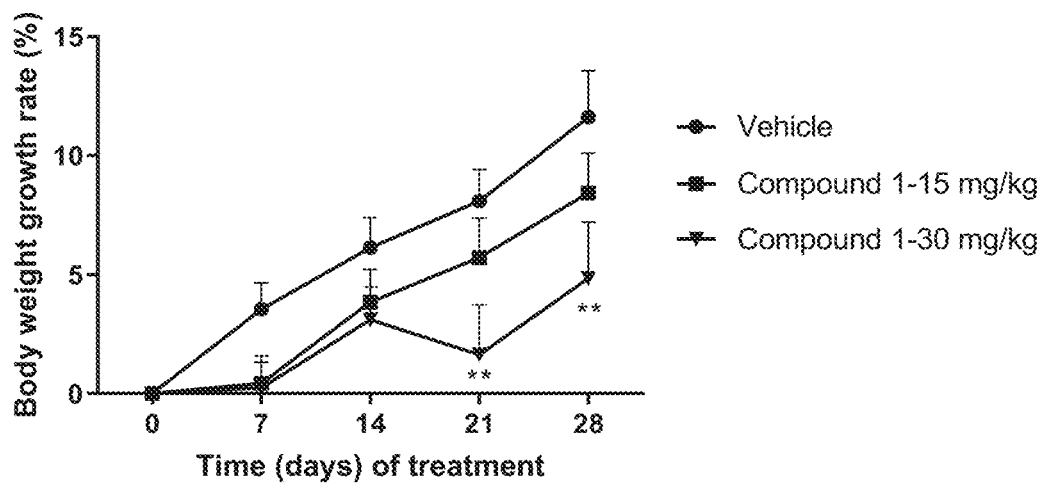

Body weight in 18-week-old DIO mice averaged 44.8±0.4 g and there were no significant differences compared to vehicle for any treatment group at baseline (44.7±0.9, 44.8±0.7 and 44.8±0.7, for vehicle, Compound 1 at 15 and 30 mg/kg, respectively). Body weight increased compared to baseline in all treatment groups during the 4-week study as shown in FIG. 6A. Although no statistically significant effects of Compound 1 on body weight were noted compared to vehicle (48.8±0.9, 47.5±1.3 and 46.0±1.2 g for vehicle and Compound 1 at 15 and 30 mg/kg, respectively) at the end of the study, Compound 1 at 30 mg/kg showed significantly lower body weight growth rate comparing to vehicle after 4 weeks of dosing (9.2±2.0%, 5.9±1.6% and 2.8±2.3% for vehicle, Compound 1 at 15 and 30 mg/kg at the end of the study, respectively) as shown in FIG. 6B.

Blood Glucose.

Blood glucose (fasted) in 18-week-old mice averaged 178.4±4.2 mg/dL and there were no significant differences compared to vehicle at study start (182.9±9.1, 185.1±8.3, and 180.1±7.0 for vehicle and Compound 1 at 15 and 30 mg/kg, respectively). Blood glucose decreased compared to baseline values in all treatment groups, including vehicle-treated mice, as the study progressed. No significant differences in blood glucose were found in all treatment groups during the whole study period (143.0±7.1, 151.9±6.1 and 137.3±4.1 mg/dL for vehicle and Compound 1 at 15 and 30 mg/kg at day 28, respectively).

OGTT.

Figure 7:
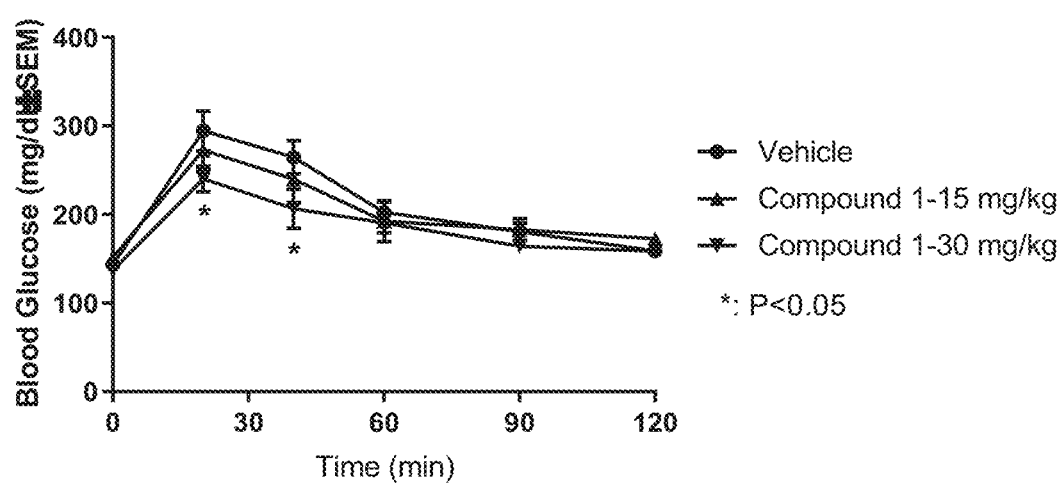
FIG. 7 shows the glucose disposal curves from an oral glucose tolerant test (OGTT) for DIO mice after 4 weeks of treatment with 15 mg/kg Compound 1, 30 mg/kg Compound 1, or vehicle: A) glucose disposal curves on Day 28 after four weeks of treatment for the three treatment groups; B) graphical depiction of the glucose AUC on Day −1 before treatment and on Day 28 after 4 weeks of treatment for the three treatment groups.
Figure 7:
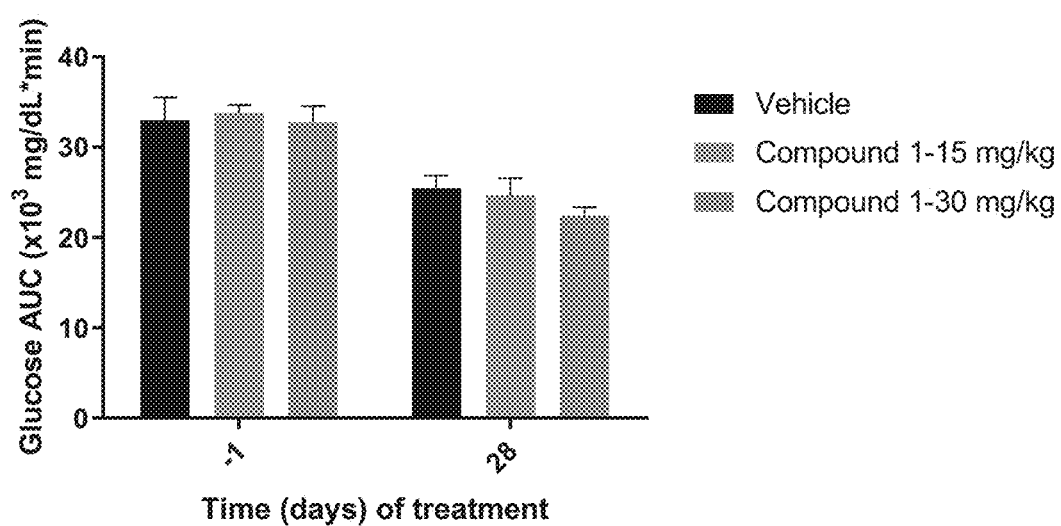

The glucose disposal curves for vehicle and Compound 1 treated mice are superimposable at baseline such that no significant differences in the glucose AUC among groups were noted (33.0±2.5, 33.8±0.9 and 32.8±1.8 mg/dL-min× $10^3$ for vehicle and Compound 1 at 15 and 30 mg/kg, respectively). Following 28 days of treatment, peak changes in the glucose disposal curves compared to vehicle are apparent for both Compound 1 treated groups as shown in FIG. 7A. However, the glucose AUCs on day 28 had no significant difference compared to vehicle for both Compound 1 treated groups, (25.5±1.4, 24.7±1.9 and 22.4±1.0 mg/dL·min× $10^3$ for vehicle and Compound 1 at 15 and 30 mg/kg, respectively).

Fasted Serum Insulin.

Figure 8:
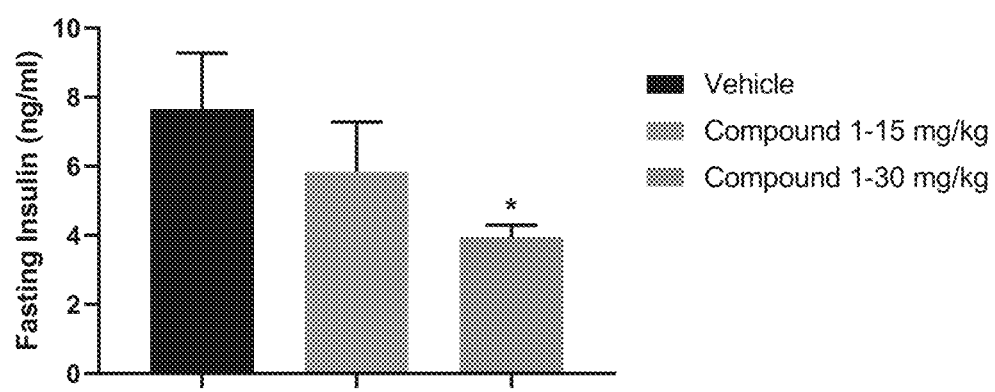
FIG. 8 shows the fasted serum insulin levels (ng/ml) for DIO mice on Day 29 after 4 weeks of treatment with 15 mg/kg Compound 1, 30 mg/kg Compound 1, or vehicle.

Fasted serum insulin averaged 5.3±0.5 ng/ml in 18-week-old DIO mice at baseline; no differences in fasted insulin were noted among treatment groups at baseline (6.1±0.6, 7.0±1.1 and 4.9±0.6 ng/ml for vehicle and Compound 1 at 15 and 30 mg/kg, respectively) as shown in FIG. 8. On day 28, fasted insulin levels were decreased in mice treated with both Compound 1 groups when vehicle group showed an increase (7.7±1.6, 5.8±1.4 and 4.0±0.3 ng/ml for vehicle and Compound 1 at 15 and 30 mg/kg, respectively). The fasted serum insulin of mice treated with 30 mg/kg Compound 1 was significantly lower comparing with mice treated with vehicle.

Summary.

Compound 1 (15-30 mg/kg/day) was generally well tolerated in the study. During the 4 weeks of treatment, mice treated with both 15 mg/kg and 30 mg/kg Compound 1 were gaining less body weight compared with vehicle-treated mice. This trend is statistically significant in mice treated with 30 mg/kg Compound 1 for 3 weeks or longer.

Blood glucose was reduced in all groups throughout the study period, and this decrease showed no significant difference among all groups. OGTT disposal curves after 4 weeks of treatment showed a decreased peak in mice treated with both 15 mg/kg and 30 mg/kg Compound 1. Hence, a slightly reduced OGTT AUC was present in these two treatment groups compared with vehicle-treated mice. However, none of these reductions in OGTT AUCs are statistically significant due to similar reduction of OGTT AUC in the vehicle group comparing with baseline. All groups had a significant reduction in OGTT AUC compared with baseline.

Compound 1 tended to reduce fasted serum insulin compared with vehicle-treated mice. The serum insulin levels of mice treated with 30 mg/kg Compound 1 were significantly lower than vehicle-treated mice on day 28 of treatment.

Example 4. Phase 1 Clinical Study of Compound 1 in Healthy Patients

Study Description.

A Phase 1, single-center, randomized, double-blind, placebo-controlled single-ascending dose (SAD) study designed to evaluate the safety, tolerability, and pharmacokinetics (PK) of Compound 1 in healthy subjects was conducted in accordance with Good Clinical Practice (GCP), the ethical principles that have their origin in the Declaration of Helsinki, and all other applicable laws, rules and regulations.

Within each dose cohort, subjects were randomized in a 3:1 ratio (6 active and 2 placebo) to receive either Compound 1 or placebo. Following Screening, subjects received single doses of study drug and were monitored during an in-clinic period and an out-patient follow-up period. Subjects were confined to the study site for Study Days −2 through 7 to collect PK and safety assessments. Following discharge from the study site on Study Day 7, subjects returned to the study site on Study Days 14, 21, 28, and 35.

Results.

A total of 36 subjects received Compound 1 (at doses in the range 1 to 40 mg) and 12 subjects received placebo. Of the original 48 subjects randomized, three discontinued for administrative reasons. A Dose Escalation Review Committee assessed all available safety and PK data from each cohort and agreed that dose escalation was appropriate in each case (up to the planned maximum dose of 40 mg).

The overall distribution of treatment-emergent adverse event (TEAEs) was comparable in each of the treatment groups with 29% (14 of 48) subjects experiencing one or more adverse events (AEs). There were no notable differences in the occurrence of AE by body system and no clear relationship of dose. The AE rate for Compound 1 subjects was somewhat lower than that in the control (placebo) subjects. Headache which was experienced by more subjects than any other AE, was only observed in one Compound 1 subject. There were no serious AEs and no discontinuations or deaths. There were no clear effects of Compound 1 on laboratory safety evaluations (clinical chemistry and hematology).

The PK of Compound 1 appeared to be well behaved with proportional increases in exposure (AUC and Cmax) with dose. The observed PK would support once daily administration of Compound 1.

Example 5. Phase 1 Clinical Study of Compound 1 in Obese Patients

A Phase 1, single-center, randomized, double-blind, placebo-controlled multiple-ascending dose (MAD) study designed to evaluate the safety, tolerability, and pharmacokinetics (PK) of Compound 1 in overweight or obese but otherwise healthy subjects is conducted in accordance with Good Clinical Practice (GCP), the ethical principles that have their origin in the Declaration of Helsinki, Title 21 of the United States Code of Federal Regulations (US CFR), Parts 50 (Protection of Human Subjects), and 56 (Institutional Review Boards), and 312 (Investigational New Drug Application), and the International Conference on Harmonization E6 (Guideline for Good Clinical Practice) (ICH E6 R2), and all other applicable laws, rules and regulations.

Within each ascending dose cohort and overall, subjects will be randomized in a 4:1 ratio (8 active and 2 placebo per cohort) to receive Compound 1 or placebo. Following Screening and Randomization, subjects will receive daily treatment with study drug for 4 weeks, with partial in-clinic confinement over the course of their participation. Subjects will be confined to the study site for Study Days −2 through 7 to collect PK and safety assessments. Following discharge from the study site on Study Day 7, subjects will continue study drug administration at home and return to the study site for outpatient study visits on Study Days 11, 14, 18, 21, 23 (±1 day). Subjects will then be confined from Study Days 27 through Study Day 33, including final dose administration on Study Day 28. Follow-up visits will be held on Study Days 42 (±2 days) and 56 (±2 days).

Five ascending dose cohorts (1 mg through 20 mg) of 10 subjects each are planned. In addition to ensuring an acceptable safety multiple for the starting dose, dose escalation will not proceed to any dose that is projected (based on an analysis of all available pK data from prior cohorts) to result in a human exposure with less than 5-fold safety multiple to the NOAEL exposure for the adverse finding of central nervous system (CNS) peri-/vasculitis in the 28-day repeated-dose dog toxicology study.

The cohorts will be enrolled independently and conducted sequentially, with dosing for successive cohorts initiating at a minimum interval of five weeks. A Dose Escalation Review Committee comprising at least the Principal or Sub-Investigator and the Sponsor Medical Monitor will assess all available interim safety and PK data from each cohort in blinded fashion to determine the appropriateness of dose escalation, after which individual subject treatment assignments may be unblinded, if necessary, to confirm any dose-limiting toxicities (DLTs). If two or more DLTs occur within the same cohort in subjects receiving active drug, dose escalation may be stopped or an intermediate dose may be tested. If dose escalation is stopped due to DLTs, the maximum tolerated dose (MTD) will be defined by the dose in the previous cohort, unless an intermediate dose is subsequently tested by the same algorithm. Dose escalation may also be halted based on a review of drug PK (e.g. if exposures do not increase between successive dose cohorts). Notably, dose escalation will not proceed to/above any dose that is projected (based on analysis of all available prior PK) to result in exposures with less than a 5-fold safety multiple to the NOAEL exposure (for finding of CNS due to peri-/vasculitis) in the 28-day repeated-dose dog toxicology study.

The interpretation of safety and tolerability, including the MTD, as applicable, will be assessed based on the collection of all available safety data, including AE/SAEs, physical examination findings, clinical laboratory parameters, vital signs, and ECGs.

The study parameters are summarized in Table 5.

TABLE 5

| | |
|---|---|
| Study Title: | A Phase 1, Single-Center, Randomized, Double-Blind, Placebo-Controlled Multiple-Ascending Dose Study to Evaluate the Safety, Tolerability, and Pharmacokinetics of Compound 1 in Otherwise Healthy Overweight or Obese Subjects |
| Development Phase: | Phase 1 |
| Study Objectives: | To assess the safety, tolerability, and MTD of MADs of Compound 1 administered orally once daily for 4 weeks, in overweight or obese but otherwise healthy subjects To characterize the repeat dose PK of Compound 1 in overweight or obese but otherwise healthy subjects |
| Study Design: | Single center, randomized, double blind, placebo-controlled, MAD |
| Sample Size: | Five ascending dose cohorts of 10 subjects each |
| Study Population: | Overweight or obese but otherwise healthy subjects |
| Investigational Product: | Immediate-release (IR) oral tablets at dose strengths of 0.5 and 5 mg |
| Control Product(S): | Matching placebo tablets |
| Safety Evaluation Criteria: | All local and systemic adverse events observed by or reported to the investigators are evaluated. The intensity, duration, and causal relationship to the study product are rated for all adverse events. |
| Statistical Methods: | Safety data, including AEs, vital signs, physical examination results, and clinical laboratory evaluations, will be summarized. Descriptive statistics will be provided, where appropriate. No statistical testing will be performed on safety data. Individual and mean plasma concentration data will be plotted over time by dose level and day and summarized descriptively at the specified time points. Pretreatment and post-treatment levels of biomarkers of insulin and glucose requirements, as well as changes from pretreatment levels, will be reported using descriptive statistics and presented graphically. Planned analyses include the following parameters: blood neutrophil elastase (NE) activity; fasting glucose, insulin, leptin, and adiponectin; HOMA-IR; glucose excursion following an OGTT (AUC glucose); and insulin excursion following an OGTT (AUC insulin). |
| Study Sites: | Single center |

Additional clinical trials with an appropriate design for the stage of clinical development may be conducted to test the efficacy of Compound 1 in the treatment of NAFLD or NASH patients. Further trials utilizing different dosage levels of the active ingredient or to differentiate between optimal doses or dosing schedules may be conducted. Further, the efficacy of the drug in specific populations, such as the elderly, children, or patients with diabetes or other pathological conditions may be determined in additional clinical trials conducted in a similar fashion.

All publications and patent applications mentioned in this specification are herein incorporated by reference to the same extent as if each individual publication or patent application were specifically and individually indicated to be incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating nonalcoholic steatohepatitis (NASH), comprising administering a therapeutically effective amount of (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile or a pharmaceutically acceptable salt, polymorph, solvate, or solvates of the salts thereof to a human patient in need of treatment for NASH, wherein the therapeutically effective amount comprises 5, 10, or 20 mg per day administered to the human patient over a period of at least 28 days.

2. The method of claim 1, further comprising administering one or more additional therapeutic agents, wherein the additional therapeutic agent is a neutrophil elastase inhibitor.

3. The method of claim 2, wherein the neutrophil elastase inhibitor is silevestat or avelestat.

4. The method of claim 1, further comprising administering one or more additional therapeutic agents, wherein the additional therapeutic agent is GFT505, seladelpar, cenecriviroc, GS-0976, GS-9674, selonsertib, or obeticholic acid.

* * * * *